US012774361B2

(12) United States Patent
Ehrmann et al.

(10) Patent No.: US 12,774,361 B2
(45) **Date of Patent: *Oct. 27, 2026**

(54) THERMOPLASTIC POLY(URETHANE-UREA) POLYADDUCTS

(71) Applicant: Technische Universität Wien, Vienna (AT)

(72) Inventors: Katharina Ehrmann, Vienna (AT); Stefan Baudis, Vienna (AT); Robert Liska, Schleinbach (AT); Markus Fitzka, Haunoldstein (AT)

(73) Assignee: TECHNISCHE UNIVERSITAET WIEN, Vienna (AT)

( * ) Notice: Subject to any disclaimer, the term of this patent is extended or adjusted under 35 U.S.C. 154(b) by 413 days.

This patent is subject to a terminal disclaimer.

(21) Appl. No.: 18/014,081

(22) PCT Filed: Jul. 5, 2021

(86) PCT No.: PCT/EP2021/068506
§ 371 (c)(1),
(2) Date: Dec. 30, 2022

(87) PCT Pub. No.: WO2022/003204
PCT Pub. Date: Jan. 6, 2022

(65) Prior Publication Data

US 2023/0272148 A1 Aug. 31, 2023

(30) Foreign Application Priority Data

Jul. 3, 2020 (EP) .................................... 20183957

(51) Int. Cl.

| | |
|---|---|
| ***C08G 18/12*** | (2006.01) |
| ***A61L 27/18*** | (2006.01) |
| ***A61L 27/50*** | (2006.01) |
| ***A61L 27/58*** | (2006.01) |
| ***A61L 31/06*** | (2006.01) |
| ***A61L 31/14*** | (2006.01) |
| ***C08G 18/08*** | (2006.01) |
| ***C08G 18/10*** | (2006.01) |
| ***C08G 18/22*** | (2006.01) |
| ***C08G 18/24*** | (2006.01) |
| ***C08G 18/32*** | (2006.01) |
| ***C08G 18/34*** | (2006.01) |
| ***C08G 18/44*** | (2006.01) |

(Continued)

(52) U.S. Cl.
CPC .............. *C08G 18/12* (2013.01); *A61L 27/18* (2013.01); *A61L 27/50* (2013.01); *A61L 27/58* (2013.01); *A61L 31/06* (2013.01); *A61L 31/14* (2013.01); *A61L 31/148* (2013.01); *C08G 18/0857* (2013.01); *C08G 18/10* (2013.01); *C08G 18/22* (2013.01); *C08G 18/244* (2013.01); *C08G 18/3215* (2013.01); *C08G 18/3221* (2013.01); *C08G 18/3228* (2013.01); *C08G 18/3246* (2013.01); *C08G 18/325* (2013.01); *C08G 18/341* (2013.01); *C08G 18/44* (2013.01); *C08G 18/4854* (2013.01); *C08G 18/73* (2013.01); *C08L 75/02* (2013.01); *C08L 75/04* (2013.01); *C08L 75/08* (2013.01); *C09D 175/02* (2013.01); *C09D 175/04* (2013.01); *C09D 175/08* (2013.01)

(58) Field of Classification Search
CPC .. C08G 18/12; C08G 18/0857; C08G 18/244; C08G 18/3228; C08G 18/325; C08G 18/341; C08G 18/10; C08G 18/22; C08G 18/3215; C08G 18/3221; C08G 18/3246; C08G 18/44; C08G 18/4854; C08G 18/73; A61L 27/18; A61L 27/50; A61L 27/58; A61L 31/06; A61L 31/14; A61L 31/148; C08L 75/02; C08L 75/04; C08L 75/08; C09D 175/02; C09D 175/04; C09D 175/08
See application file for complete search history.

(56) References Cited

FOREIGN PATENT DOCUMENTS

| | | | | |
|---|---|---|---|---|
| CA | 2040910 A1 * | 10/1991 | ............. | C08G 18/75 |
| EP | 0452775 A2 | 10/1991 | | |

(Continued)

OTHER PUBLICATIONS

International Search Report and Written Opinion issued Nov. 2, 2021 in International Application No. PCT/EP2021/068506.

(Continued)

*Primary Examiner* — Rabon A Sergent
(74) *Attorney, Agent, or Firm* — Panitch Schwarze Belisario & Nadel LLP

(57) ABSTRACT

A thermoplastic poly(urethane-urea) polyadduct with sterically hindered urea groups of the following Formula (I):

$$—[I—M—(I—C_1)_a—(I—M)_b—(I—C_2)_c]_n— \quad (I)$$

I, M, $C_1$ and $C_2$ each representing bivalent residues linked to each other via a urethane or urea moiety. In the residues I, $C_1$ and $C_2$, when more than four carbon atoms are present, optionally at least one of them is substituted by a heteroatom selected from oxygen and nitrogen. Optionally at least one of the residues I, M, $C_1$ and $C_2$ includes one or more ester moieties. a, b and c each independently represent an integer from 0 to 10, and n is a number ≥3 representing the number of blocks in the polyadduct. Within each separate block a+c≥1, and in all blocks together at least one a≥1 and at least one c≥1.

15 Claims, 10 Drawing Sheets

(51) Int. Cl.

| | |
|---|---|
| ***C08G 18/48*** | (2006.01) |
| ***C08G 18/73*** | (2006.01) |
| ***C08L 75/02*** | (2006.01) |
| ***C08L 75/04*** | (2006.01) |
| ***C08L 75/08*** | (2006.01) |
| ***C09D 175/02*** | (2006.01) |
| ***C09D 175/04*** | (2006.01) |
| ***C09D 175/08*** | (2006.01) |

(56) References Cited

FOREIGN PATENT DOCUMENTS

| | | | | | |
|---|---|---|---|---|---|
| WO | WO-2005089778 | A1 | * | 9/2005 | ........... A61K 31/785 |
| WO | WO-2017155958 | A1 | * | 9/2017 | ............. A61K 47/34 |

OTHER PUBLICATIONS

Ying et al., "Hydrolyzable Polyureas Bearing Hindered Urea Bonds," Journal of the American Chemical Society, vol. 136, pp. 16974-16977 (2014).

* cited by examiner 2,5-Dimethylpiperazine model molecule

THERMOPLASTIC POLY(URETHANE-UREA) POLYADDUCTS

CROSS-REFERENCE TO RELATED APPLICATIONS

This application is a Section 371 of International Application No. PCT/EP2021/068506, filed Jul. 5, 2021, which was published in the German language on Jan. 6, 2022 under International Publication No. WO 2022/003204 A1, which claims priority under 35 U.S.C. § 119(b) to European Application No. 20183957.8, filed Jul. 3, 2020, the disclosures of which are incorporated herein by reference in their entireties.

The present invention relates to new thermoplastic poly (urethane-urea) polyadducts.

STATE OF THE ART

In numerous processing methods of polymers, such as extrusion, injection molding, blow molding, solution casting, spin coating and other thermal and solution-based manufacturing methods, basic requirements include low viscosities of polymer melts or solutions at the lowest possible temperatures or good solubility of the polymers in conventional solvents. However, polymers having these desirable properties are often not sufficiently mechanically resistant for their later use because, for achieving these properties before processing, practically no chemical crosslinking and only limited physical crosslinking may be present. For example, thermoplasts are basically well suited for the above processing methods due to their generally low melting viscosity at low to moderate temperatures, however, have only limited mechanical resistance.

To improve the physical properties of these polymers, processed polymers are often subjected to postprocessing to subsequently introduce chemically or physically induced crosslinking. However, the latter crosslinking methods (e.g., thermal or light-based) require large amounts of energy and/or expensive equipment, and chemical methods (e.g., gas or liquid phase crosslinking) normally use chemicals (e.g., thiols or alkali metal hydrides) that are sometimes expensive and require adherence to various safety requirements during their use.

Polymers that often show quite good mechanical properties include, for example, polyurethane/polyurea thermoplasts, which are usually produced by polyaddition of diols and diamines with diisocyanates and are hereinafter referred to as thermoplastic poly(urethane-urea) adducts or TPUUs ("thermoplastic polyurethane-ureas). The structure of such adducts can generally be represented by the following Formula (1):

$$—[(I—A)_a—(I—B)_b]_n— \qquad (1)$$

wherein I, A and B each represent bivalent residues derived from a diisocyanate (I), a diol (A) or a diamine (B) and linked to each other via a urethane or urea moiety, a and b represent the respective number of repeats of the urethane or urea units, and n represents the number of blocks comprising the two. A more detailed exemplary representation of a structure with alternating diol units A and diamine units B, i.e., with a=b=1, is the following Formula (2):

(2)

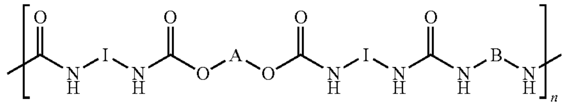

Therein, in addition, two urethane moieties, —NH—CO—O— and —O—CO—NH—, derived from the addition of a diol, HO-A-OH, to two diisocyanate molecules alternate with two urea moieties, —NH—CO—NH—, derived from the addition of a diamine, $H_2N—B—NH_2$, to two diisocyanates. If a and b represent numbers >1, polyurethane and polyurea segments alternate within a block.

A representation using secondary diamines for forming the urea units is somewhat more complex because, in these cases, two further residues attached to the nitrogen atoms have to be taken into account in addition to residue B. For example, a N,N'-dimethyl derivative of the above diamine would result in a structure according to the following Formula (3):

(3)

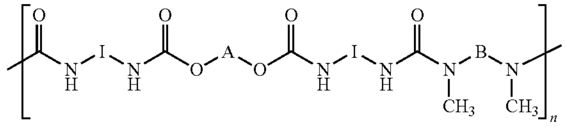

The general structure could be represented in a simplified way by referring to the bivalent residue, $—NCH_3—B—NCH_3—$, obtained by removing the two N-linked hydrogen atoms of the diamine as residue D, as shown in Formula (4):

$$—[(I—A)_a—(I—D)_b]_n— \qquad (4)$$

In this case, a combination of the two representations results in a structure of the following Formula (5):

(5)

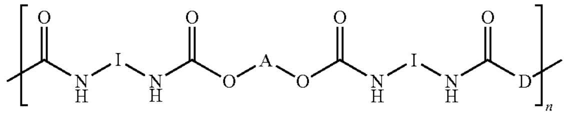

wherein the two nitrogen atoms of residue D each complete an N-methylated urea moiety.

The mechanical properties of TPUUs can be controlled within relatively large ranges by selecting suitable monomers, e.g., by providing a suitable ratio of hard and soft segments within the polymer chains. For example, EP 452,775 A2 discloses the production of TPUUs with increased heat resistance using 4,4'-diisocyanatodicyclohexylmethane and optionally methylated piperazine for producing polyurea hard segments, which are combined with polyurethane soft segments made from macrodiols.

In addition, it has been known for decades that, in sterically hindered urea molecules, the stability of the bond between nitrogen atoms substituted with at least one voluminous residue and the carbonyl group is instable. The dissociation of urea molecules with different bulky substituents was already described in 1974, including various combinations of isopropyl, sec-butyl, tert-butyl, 3-pentyl, cyclohexyl and isooctyl substituents on the same nitrogen atom as well as a cyclic variant using tetramethylpiperidine (Stowell, J. C., Padegimas, S. J., "Urea dissociation. Measure of steric hindrance in secondary amines", J. Org. Chem. 39(16), 2448-2449 (1974)).

The equilibrium reaction taking place in this case can be represented, for example, as shown in the following Scheme A for a double substitution with tert-butyl:

Scheme A

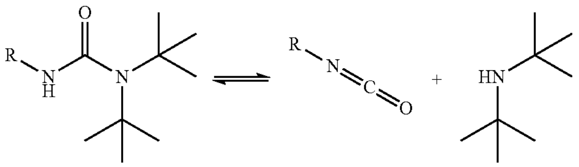

This scheme illustrates that the instable bond between the carbonyl group and the sterically hindered nitrogen atom of the secondary amine is reversibly cleaved under certain conditions, thus forming an isocyanate and the free secondary amine, i.e., the original urea is also reformed, with the equilibrium state strongly depending on the selection of the two substituents on the sterically hindered nitrogen atom.

Sterically hindered urea groups were subsequently used, among other things, for masking isocyanates, and Hutchby et al., for example, examined the methanolysis of ureas N-substituted with methyl, ethyl, isopropyl and tert-butyl at temperatures between 20° C. and 70° C. (Hutchby, M., Houlden, C. E., Ford, J. G., Tyler, S. N. G., Gagné, M. R., Lloyd-Jones, G. C., Booker-Milburn, K. I., "Hindered ureas as masked isocyanates: facile carbamoylation of nucleophiles under neutral conditions", Angew. Chem. Int. Ed. 48(46), 8721-8724 (2009)).

The first use of this reaction in macromolecules for developing "dynamic" materials was described by Ying et al. (Ying, H., Zhang, Y., Cheng, J., "Dynamic urea bond for the design of reversible and self-healing polymers", Nat. Commun. 5, 3218 (2014)). Here, 2,2,6,6-tetramethylpiperidine carboxylic acid amide and 1-tert-butyl-1-isopropyl-, 1-tert-butyl-1-ethyl-, 1,1-diisopropyl- and 1,1-diethylurea were used for molecular kinetics studies. In addition, a simple polyurea molecule was produced from 1,3-bis-(isocyanatomethyl)cyclohexane and N,N'-di-tert-butylethylenediamine and crosslinked polyurethane-urea polymers were produced from triethanolamine, hexamethylene diisocyanate, tetraethylene glycol, and four different sterically hindered diamines and examined, showing so-called "self-healing effects" of the crosslinked polymer materials, which were, however, always accompanied by a tensile strength decrease due to the self-healing.

Subsequently, numerous further experiments with corresponding "self-healing" polymers were conducted. For example, Zhang et al. used different ethanolamines, namely 2-tert-butylaminoethanol, 2-isopropyl-aminoethanol und N-butylaminoethanol, for producing so-called "recyclable" poly(urethane-urea) duroplasts (Zhang, Y., Ying, H., Hart, K. R., Wu, Y., Hsu, A. J., Coppola, A. M., Kim, T. A., Yang, K., Sottos, N. R., White, S. R., Cheng, J., "Malleable and recyclable poly(urea-urethane) thermosets bearing hindered urea bonds", Adv. Mater. 28(35), 7646-7651 (2016)). However, the recycled polymer materials reached the original tensile strength rates at best. Furthermore, Zhang et al. described again the use of ethanolamines as chain extenders for dynamic poly(alkylurea-urethane) networks with improved stress relief (Zhang, L., Rowan, S. J., "Effect of sterics and degree of cross-linking on the mechanical properties of dynamic poly(alkylurea-urethane) networks", Macromolecules 50(13), 5051-5060 (2017)). Bruce und Lewis examined glass transition temperatures of self-healing poly (urethane-urea)s for the production of less soft materials having the same self-healing mechanism (Bruce, A. C., Lewis, C. L., "Influence of glass transition temperature on mechanical and self-healing behavior of polymers bearing hindered urea bonds", SPE ANTEC, Anaheim, 2017; Anaheim, 2017), and two further articles relate to the use of sterically hindered diamines (in particular N,N'-di-tert-butylethylenediamine) as chain extenders for the production of reprocessable poly(urethane-urea) duroplasts with shape memories (Fang, Z., Zheng, N., Zhao, Q., Xie, T., "Healable, reconfigurable, reprocessable thermoset shape memory polymer with highly tunable topological rearrangement kinetics", ACS Appl. Mater. Interfaces 9(27), 22077-22082 (2017); Wang, Y., Pan, Y., Zheng, Z., Ding, X., "Reconfigurable and reprocessable thermoset shape memory polymer with synergetic triple dynamic covalent bonds", Macromol. Rapid Commun. 39(10), 1800128 (2018)).

Of course, corresponding disclosures of such "self-healing" polymers can also be found in patent literature, in particular from the above authors as inventors; see, e.g., WO 2014/144539 A2, WO 2016/069582 A1, WO 2016/126103 A1, and WO 2016/126756 A1.

However, in aqueous environments, the isocyanate resulting from the reaction shown in Scheme A undergoes a hydrolysis to the corresponding carbamic acid, which is subsequently prone to spontaneous decarboxylation, as is shown in Scheme B below:

Scheme B

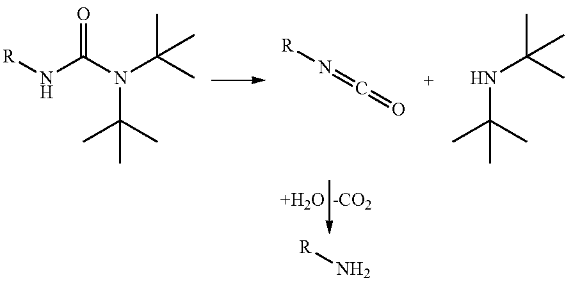

This leads to the two free amines that had initially formed the urea molecule. Such an in situ formation of isocyanates from sterically hindered urea molecules and subsequent hydrolysis of the isocyanates in an aqueous medium allows, among other things, the hydrolysis of polyureas.

For macromolecules, this reaction sequence was first disclosed by Ying et al. (Ying, H., Cheng, J., "Hydrolyzable polyureas bearing hindered urea bonds", J. Am. Chem. Soc. 136(49), 16974-16977 (2014)), where polyureas and crosslinked poly(urethane-urea) organogels were dissolved in DMF and then hydrolyzed with water, and further works gave evidence for the biocompatibility of hydrogels containing sterically hindered urethane groups for hydrolysis (see Ying, H., Yen, J., Wang, R., Lai, Y., Hsu, J.-L.-A., Hu, Y., Cheng, J., "Degradable and biocompatible hydrogels bearing a hindered urea bond", Biomater. Sci. 5(12), 2398-2402 (2017)). Later, Cai et al. examined the hydrolysis of a polyurea dissolved in THF with 5% (vol/vol) water and provided evidence for a pH independence of the hydrolysis reaction (Cai, K., Ying, H., Cheng, J., "Dynamic Ureas with fast and pH-independent hydrolytic kinetics", Chem. Eur. J. 24(29), 7345-7348 (2018); and WO 2017/155958 A1), and recently Chen et al. disclosed the use of polyureas with sterically hindered urea groups for drug release (Chen, M., Feng, X., Xu, W., Wang, Y., Yang, Y., Jiang, Z., Ding, J., "PEGylated polyurea bearing hindered urea bond for drug delivery", Molecules 24(8), 1538 (2019)), where several PEGylated polyureas dissolved in DMSO were used for creating micelles around an anti-tumor agent (Paclitaxel); the micelles were dissolved in PBS and injected into tumors of experimental animals, where the active agent was released via hydrolysis of the polyurea molecules.

In all published experiments regarding "self-healing" or "postprocessing" of polyureas and poly(urethane-ureas), of which a great majority only comprises the reversible reaction according to Scheme A and only a few also mention a subsequent hydrolysis reaction, individual mechanical properties were, in rare cases, partially improved, such as the above poly(urethane-ureas) (PUUs) with improved stress relief according to Zhang et al., but mostly modified polymers with worse properties than before or at best the same were obtained. In addition, thermoplastic polyureas, polyurethanes or poly-(urethane-urea) polyadducts (TPPUs) have never before been specifically examined under this aspect, and consequently not a single case reported modified polymers with properties that would be better suited for the thermomechanical processing methods mentioned at the beginning.

In addition, a combination of various desirable properties would be advantageous for certain application areas of thermoplasts, such as good thermomechanical properties of the polymer materials, before and after their processing, good solubility of the starting material to allow or simplify solution-based processing methods, and sometimes biocompatibility of the material to guarantee its usability in contact with a human or animal body. TPUUs characterized by such property combinations, however, have not been known until now.

Thus, the object of the invention was to develop a new thermoplastic poly(urethane-urea) (TPPU) material with self-healing properties based on sterically hindered secondary amines, which shows improved thermomechanical properties after reaction in an aqueous environment and is thus better suited for use in corresponding processing methods than known materials according to the state of the art and shows good solubility as well as biocompatibility to be apt for use in biomedical applications.

DISCLOSURE OF THE INVENTION

The present invention achieves this object by providing a thermoplastic poly(urethane-urea) (TPUU) polyadduct with sterically hindered urea groups of the following formula (I):

$$—[I—M—(I—C_1)_a—(I—M)_b—(I—C_2)_c]_n— \qquad (I)$$

wherein I, M, $C_1$ and $C_2$ each represent bivalent residues that are linked to each other via a urethane or urea moiety, whereof each I independently represents a bivalent, saturated or unsaturated, aliphatic, alicyclic or aromatic residue with 1 to 20 carbon atoms derived from a diisocyanate;

each M independently represents a bivalent residue of an aliphatic polyether, polyester or polycarbonate derived from a macrodiol having a number average molecular weight $M_n \geq 500$;

each $C_1$ independently represents a bivalent, saturated or unsaturated, aliphatic or alicyclic residue with 1 to 30 carbon atoms derived from a diamine or amino alcohol with at least one sterically hindered secondary amino group by removing one N-linked hydrogen atom each of the diamine or one N-linked and the O-linked hydrogen atoms of the amino alcohol;

each $C_2$ independently represents a bivalent, saturated or unsaturated, aliphatic, alicyclic or aromatic residue with 1 to 20 carbon atoms derived from a diol, diamine or amino alcohol;

wherein, in the residues I, $C_1$ and $C_2$, when more than four carbon atoms are present, optionally at least one of them is replaced by a heteroatom selected from oxygen and nitrogen;

wherein optionally at least one of the residues I, M, $C_1$ and $C_2$ comprises one or more ester moieties; and a, b and c each independently represent an integer from 0 to 10, and n is a number ≥3 representing the number of blocks in the polyadduct;

provided that within each separate block a+c≥1 and in all blocks together at least one a≥1 and at least one c≥1.

The inventors of the subject matter of the present application have surprisingly found for such thermoplastic poly (urethane-urea) (TPUU) polyadducts with sterically hindered urea groups that these macromolecules not only show the reaction shown in Scheme B in a solution or as a hydrogel, as had been known from the state of the art, but also in a solid state on contact with water or in an aqueous environment—even after the material has been processed to solid products, such as by solution casting, foil drawing or the like.

In addition, it was even more surprising that, when using the inventive TPUUs in a solid state, the isocyanate formed by opening the unstable urea bond is apparently not completely hydrolyzed to a free amine, as previously shown in Scheme B, but that a part of the isocyanate reacts with a part of the free amine formed by hydrolysis, forming a new, not sterically hindered urea moiety, which results in stable polymer chains with improved thermomechanical properties, as will be shown in the examples below. While not wishing to be bound by theory, the inventors assume that the presence of this reaction—herein referred to as "recombination reaction"—of a decarboxylated isocyanate with a not yet decarboxylated one is due to the lower reaction rate of the hydrolysis reaction of the polymer chains in a solid phase. The following Scheme C shows such a reaction sequence—analogous to Scheme B—for a terminal, sterically hindered urea group:

Scheme C

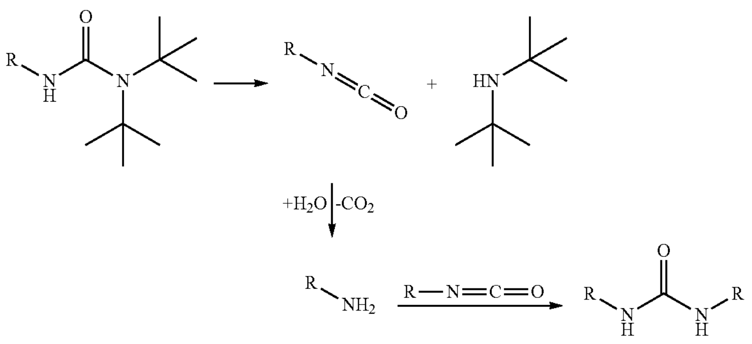

And the following Scheme D for two urea moieties within a TPUU polymer chain, which moieties are derived from the same secondary diamine sterically hindered on both sides, in the present case from N,N'-di-tert-butylpropylenediamine:

Scheme D

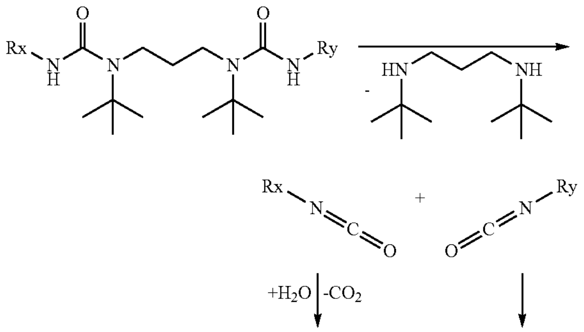

-continued

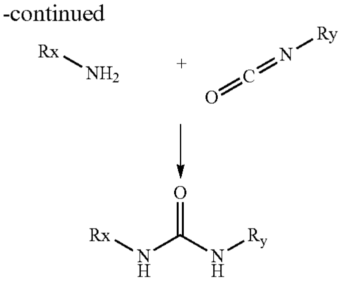

Thereby, on contact of the TPUU with water, a new TPUU polymer is formed, which polymer formally results from the elimination of a diamine sterically hindered on both sides and a carbonyl group from the backbone of the polymer.

The reaction of TPUUs containing residues of diamines sterically hindered on only one side or amino alcohols is shown in the overleaf Scheme E, wherein X represents O (derived from an amino alcohol) or NH (derived from a diamine):

Scheme E

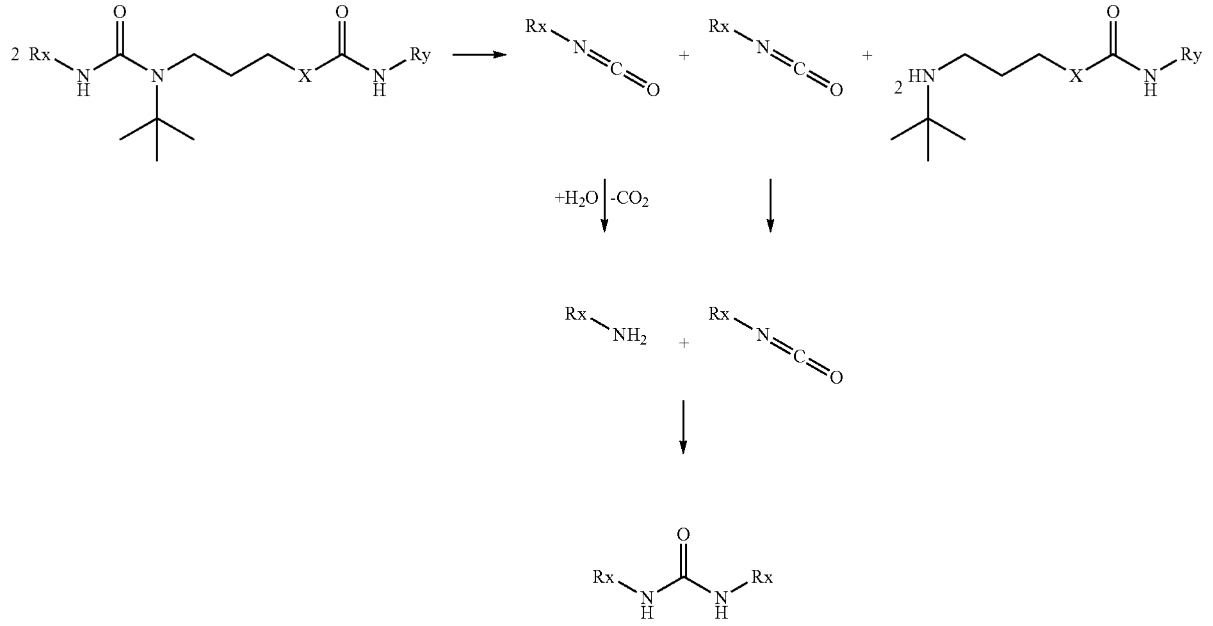

In this case, by opening the bonds of one sterically hindered urea moiety each of two TPUU polymer chains, two polymeric isocyanates Rx-N═C═O are formed, one of which undergoes hydrolysis and decarboxylation, as known, to a free amine, Rx-$NH_2$, in the presence of water, subsequently, however, adds to the second isocyanate that is not decarboxylated yet and thus forms a new, stable TPUU polymer with double the chain length of the residue Rx-NH—. In addition, two new TPUU polymers with terminal, sterically hindered secondary amino groups shortened by the length of Rx compared to the starting molecule are formed, which polymers optionally undergo the "self-healing" back reaction with one of the isocyanates to the instable starting polymer as known from the state of the art, but are not able to form stable urea bonds with isocyanates.

In this way, in an aqueous environment, new polymers are formed from the inventive solid-state TPUUs, which polymers may have longer chain lengths (Scheme C), substantially the same chain length (Scheme D) or longer as well as shorter chain lengths (Scheme E) than the starting molecules, depending on the position of the opening instable bond(s) within the backbone, however, in all cases comprise only stable urea bonds that are not sterically hindered after reaction with water.

In contrast thereto, only shorter molecules are formed from aqueous solutions of polyureas examined in the past because the hydrolysis and subsequent decarboxylation of the isocyanates formed by opening instable, sterically hindered urea bonds is much faster in a solution so that they are not stable long enough to undergo a reaction with a free amine. The exemplary reaction of solid-state TPUUs according to the present invention on contact with water shown in Scheme D above, which results in a free secondary diamine sterically hindered on both sides and a "recombinated" polyurea chain shortened by the length of the diamine and a carbonyl group, would, in a solution, result in only two polymeric free amines in addition to the released sterically hindered diamine, which, of course, cannot undergo any reaction, as is shown in the following Scheme F:

Scheme F

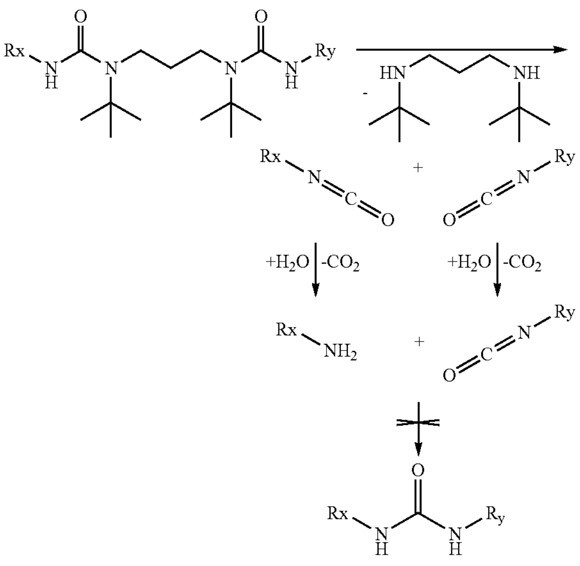

This leads to the formation of two new polymers, the molecular weights of which are, depending on the position of the residue derived from the sterically hindered secondary diamine within the original polymer chain, lower than those of the starting polymer, sometimes considerably lower, up to approximately 50% reduction. This is one of the reasons why almost all relevant prior art documents on the behavior of "self-healing" polyureas in aqueous solutions report equal thermomechanical properties of the resulting shorter polymers at best, but usually deteriorated ones.

In addition, however, the new polymers, Rx-NH—CO—NH-Ry, resulting according to Scheme D from inventive solid-state TPUUs on contact with water (or an aqueous environment) have—assuming that only one sterically hindered diamine was contained in the polymer chain—not only practically the same molecular weight as before treatment with water. They also contain a new urea moiety, the two hydrogen atoms of which are not shielded by bulky residues and are therefore able to form hydrogen bridges to urea or urethane moieties of a further, adjacent polymer chain. While not wishing to be bound by theory, these hydrogen bonds are, according to the opinion of the inventors, the main reason for the improvement of the thermomechanical properties because this effect surprisingly occurs—as will be shown in the examples below—even when a plurality of sterically hindered urea moieties is contained within the chains of inventive TPUUs so that "recombination reactions" always form new chains with (sometimes considerable) lower molecular weights.

When processed to solid products, for example, inventive TPUUs show better extensibility and tensile strength values as well as higher melting points after storing the products in water for only a few hours compared to immediately after processing. At the same time, however, solubility was higher before water treatment, which guarantees that the starting polymers can be processed more easily.

Furthermore, partly due to the optional presence of ester moieties in the chains of the inventive TPUUs, which is preferred according to the invention, the starting polymers as well as the reaction products formed by "recombination" in a suitable aqueous environment, e.g., under physiological conditions, are cleavable (e.g., also enzymatically), which offers the advantage of biological degradability. Consequently, solid products made from the inventive TPUUs are also suited very well for medical purposes, such as body implants or other applications requiring a temporal limitation of their presence within the body.

The components of the inventive TPUUs contained in Formula (I) are represented by abbreviations, as is common in polyurethane and polyurea chemistry, with "I" for isocyanate, "M" for macrodiol and "$C_1$" and "$C_2$" for two different types of chain extenders which contain amino or OH groups and serve as hard segments for linking isocyanate and macrodiol building blocks via corresponding urethane and/or urea bonds. Of these two chain extenders, $C_1$, being a diamine hindered on one or both sides or an amino alcohol with a sterically hindered secondary amino group, as defined above, serves for forming the instable urea bond cleavable in an aqueous environment. And $C_2$ serves, on the one hand, as further hard segment for additionally linking macrodiol building blocks and thus for controlling the chain length between the sterically hindered urea groups formed by $C_1$, and, on the other hand, in preferred embodiments additionally for promoting biological degradability of the inventive TPUUs by selecting diamines, diols or amino alcohols, respectively, which contain an ester moiety cleavable under physiological conditions, as monomeric building blocks for introducing $C_2$ into the TPUU chain. This is particularly advantageous when a polyether without cleavable carboxylate or carbonate ester moieties is selected as macrodiol.

In preferred embodiments, an inventive thermoplastic TPUU is characterized by one or more of the following parameters:

a and c are each independently ≤5 or ≤3; and/or
a and c are each independently ≥1; and/or
b≥1; and/or
b=c or b=a or b+1=a+c; and/or
n≥5 or n≥10 or n≥50.

Here, relatively low values of a and c result in a comparatively high proportion of units M derived from macrodiols, i.e., soft segments, in the TPUUs according to the invention, which provides for low melting points of the polymers and high flexibility, even at relatively low temperatures, as well as a not overly large number of instable urea bonds in the entire polymer in order not to obtain reaction products with extremely short chains after reaction of the processed TPUUs in an aqueous environment.

If a and c are both ≥1, each block contains at least one sterically hindered urea group formed by $C_1$ as well as a further chain extender $C_2$, which preferably comprises a cleavable ester moiety.

In TPUUs of Formula (I) with b≥1, which is preferably true for the case that a and c are each independently ≥1, the two chain extender units, $C_1$ und $C_2$, are separated by at least one macrodiol unit. This improves controllability of the distance between these units and allows, in particularly preferred embodiments, the provision of a relatively large distance between sterically hindered urea moieties in $C_1$ and preferred cleavable ester moieties in $C_2$, so that during use of the inventive TPUUs, when processed to solid products, and the reactions of the free amines with non-decarboxylated isocyanate moieties occurring in this case, the ester moieties are not prematurely cleaved due to attacks by the free amines.

Embodiments in which b=c or b=a or b+1=a+c mainly offer advantages during the production of the inventive TPUUs of Formula (I). For example, in the first two cases, an oligomer or prepolymer with alternating chain extender units $C_1$ or $C_2$ and macrodiol units M linked via diisocyanates can be produced by mixing the corresponding sterically hindered diamine or amino alcohol (for $C_1$) or the not sterically hindered diamine or amino alcohol or diol (for $C_2$) with an equimolar amount of a macrodiol with a small molar excess of diisocyanate before the reaction product is reacted with the respectively desired molar amounts of the other chain extender and of diisocyanate. In the case of b+1=a+c, on the one hand, two such oligomers or prepolymers, each containing one chain extender alternating with macrodiol units, can easily be produced separately and then linked to each other via a diisocyanate. On the other hand, in particularly preferred embodiments in which a, b and c are each 1, equimolar amounts of the monomeric building blocks providing the two chain extenders $C_1$ and $C_2$ can be reacted with the double amount of macrodiol and the quadruple amount of diisocyanate (or preferably a small excess of diisocyanate), i.e., in a ratio $C_1$:$C_2$:M:I of 1:1:2:4 (or preferably >4, e.g., 4.02 or 4.03), which simplifies synthesis. The latter can, in some cases, also be conducted as "one-pot polyaddition", in which cases, however, the reactivities of the diamines, amino alcohols or diols introducing the chain-extending residues $C_1$ and $C_2$ into the inventive TPUUs have to be taken in to account. If the difference between their reactivities is too large, since at least one sterically hindered amine is present as reactant, sometimes only polyadducts with relatively short chains are obtained when all reactants are mixed simultaneously, which is usually not preferred.

For a skilled person, this option with regard to the polymerization reaction sequence means that the order of components within a block, in particular of the components $C_1$ and $C_2$, is not limited to that explicitly shown in Formula (I). This means that with values of a and c of >1 each, even if a=c, the two building blocks containing one chain extender each, (I—$C_1$) and (I—$C_2$), do not have to alternate within a block in all cases but can also be distributed statistically.

The number of blocks n in the inventive TPUUs and thus their number-average molecular weights are not particularly limited and can be freely chosen depending on the respective intended use and the thermomechanical or other physical properties desirable therefor. As well known to the skilled person, the chain length of polyadducts mainly depends on the stoichiometry of the monomeric and prepolymeric building blocks during the polyaddition reactions. As preferred according to the present invention, the number of blocks n is ≥5, more preferably ≥10, and in particular ≥20, ≥50, or ≥100, in order to guarantee that the inventive TPUUs are suitable for a plurality of different thermomechanical or solution-based processing methods.

In particularly preferred embodiments, the inventive TPUUs are characterized by the fact that at least one of the residues I, M, $C_1$ and $C_2$ comprises one or more ester moieties cleavable under physiological conditions, and that the residues I, M, $C_1$ and $C_2$ as well as any cleavage products thereof are biocompatible and physiologically acceptable. For example, this allows their use in the production of implants that are decomposed within the body of a patient in the course of time without causing any damage.

The diisocyanates usable for the production of the inventive TPUUs are not particularly limited according to the invention as long as the resulting units I each have 1 to 30 carbon atoms. In preferred embodiments, these residues I are each independently derived from a diisocyanate selected from the following group: 1,6-hexamethylene diisocyanate, 4,4'-diisocyanatodicyclohexylmethane (4,4'-methylenedi (cyclohexyl iso-cyanate), $H_{12}$MDI), isophorone diisocyanate, 1,3-bis(isocyanatomethyl)cyclohexane, diphenylmethane-4,4'-diisocyanate (4,4'-diisocyanatodiphenylmethane; methylene-di(phenyl isocyanate), MDI), L-lysine ethyl ester diisocyanate, because these compounds have advantageous structures, are physiologically acceptable, and are commercially available at relatively low prices.

Similar considerations apply to the macrodiols for introducing the units M into the inventive TPUUs. These are, apart from a number-average molecular weight $M_n$≥500 of the units M for providing the polyadducts with suitable molecular weights and thermoplasticity, not particularly limited. Preferably, the residues M are, however, each independently derived from a polyether, polyester or polycarbonate from the following group: polytetrahydrofuran, polyethylene glycol, polypropylene glycol, polycaprolactone, polylactide, polyglycolide, poly(lactide-co-glycolide) and polyhexamethylene carbonate, more preferably those with a number-average molecular weight $M_n$≥800, in particular ≥1,000. These are physiologically acceptable, commercially available or easily synthesizable and have well-known properties via which the properties of the inventive TPUUs can be easily controlled.

The diamines or aminoalcohols used for introducing the bivalent residues with at least one sterically hindered secondary amino group each are not particularly limited, either, as long as they have only saturated or unsaturated, aliphatic or alicyclic residues with 1 to 30 carbon atoms in total in addition to the two nitrogen atoms or the nitrogen atom and the oxygen atom. Herein, this includes all carbon atoms of all residues that are linked to the nitrogen atom(s) of the aminoalcohol or diamine with (at least) one sterically hindered secondary amino group each, i.e., of the bivalent residue $R_1$ linking the two amino groups or the amino and hydroxyl groups as well as of the substituent $R_2$ on the nitrogen atom of the secondary amino group(s), as shown in the following Formulas (II) (diamine) and (III) (aminoalcohol):

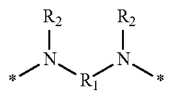
(II)

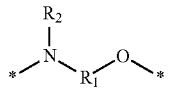
(III)

wherein the bonds marked with asterisks each show the linkage to the carbonyl group of a urethane or urea moiety linking the residues I, M, $C_1$ and $C_2$, and at least one of the residues $R_1$ and $R_2$ is a bulky residue causing sterical hinderance of the urea moiety, to which the respective nitrogen atom belongs, within the TPUU. In the case of diamines with only one secondary amino group, one of the residues $R_2$ in Formula (II) is hydrogen, and in the case of diamines with two sterically hindered secondary amino groups, either at least residue $R_1$ in Formula (I) (and optionally also one or both of the residues $R_2$) is a bulky residue, or both residues $R_2$ (and optionally also residue $R_1$) are bulky residues.

In preferred embodiments of the inventive TPUUs, however, the residues $C_1$ are not derived from aminoalcohols, but from secondary diamines sterically hindered on both sides, in order to allow the recombination reactions shown in Scheme D above. More preferably, they are selected from residues of the above Formula (II), wherein at least the two residues $R_2$ and optionally also residue $R_1$ are bulky residues. In the residues of the above Formula (II), the two $R_2$ are preferably independently selected from univalent, bulky, saturated or unsaturated, aliphatic or alicyclic residues with 1 to 10 carbon atoms, wherein the two residues $R_2$ are optionally linked to each other to form a ring which comprises the two nitrogen atoms, $R_1$, and at least one carbon atom each of the two residues $R_2$; provided that the ring is not piperazine, 2-methylpiperazine or 2,5-dimethylpiperazine.

The reasons for the exception of piperazine, 2-methylpiperazine or 2,5-dimethylpiperazine is, on the one hand, that these three diamines are known for the production of TPUUs from the disclosure of EP 452,775 A2 mentioned above (even if, in fact, only TPUUs with unsubstituted piperazine were produced), and on the other hand, that these three compounds are not diamines with sterically hindered secondary amino groups in the sense of the present invention. This is evidenced by the examples and reference examples below, where neither urea groups produced with piperazine nor with 2,5-dimethylpiperazine showed any significant measurable reactivity during one week of contact with a primary amine—neither at room temperature nor at elevated temperatures. In contrast, amino groups substituted with tert-butyl and thus sterically hindered according to the present invention, which, as described above, form instable bonds between the carbonyl group of the urea and the sterically hindered nitrogen atom of the secondary amine, show significant changes of the urea groups after mixing with the primary amine after only 24 h wet storage at room temperature. And even with secondary amino groups being substituted with isopropyl and thus less sterically hindered, a more than 50% higher tensile strength was recognizable after 24 h wet storage compared to dry storage, at least after an increase of the temperature (e.g., to 60° C.) to increase reactivity, as will be shown in Example 14 below.

In even more preferred embodiments, the residues $C_1$ are selected from residues of the above Formula (II), wherein $R_1$ is selected from bivalent, saturated or unsaturated, aliphatic or alicyclic residues with 1 to 20 carbon atoms, more preferably from $C_1$-$C_{10}$-alkylene or $C_4$-$C_{10}$-cycloalkylene residues, in particular from $C_2$-$C_6$-alkylene or $C_5$-$C_6$-cycloalkylene residues; and/or the $R_2$ are each independently selected from 1,1-dimethyl-substituted, saturated or unsaturated $C_1$-$C_6$-alkyl residues or 1-methyl-substituted $C_3$-$C_6$-cycloalkyl residues, in particular from isopropyl, tert-butyl, 1,1-dimethylpropyl or 1-methylcyclohexyl.

These preferred selection options from residues of secondary diamines sterically hindered on both sides and having relative short chains result in having short-chain hard segments $C_1$ in the inventive TPUUs compared to the soft segments M with higher molecular weights, which promotes thermoplasticity of the polymers and subsequently also the probability of the "recombination reaction" according to the above Scheme D during contact of the solid products produced from the TPUUs with water. In addition, they are also considered physiologically acceptable.

Furthermore, the selection of the additional chain extender units, $C_2$, is not particularly limited, either, as long as they are saturated or unsaturated, aliphatic, alicyclic or aromatic residues with 1 to 20 carbon atoms derived from a diol, diamine or aminoalcohol. These diamines or aminoalcohols for introducing $C_2$ into the TPUUs of the invention are, however, —and contrary to $C_1$—not sterically hindered amines and in addition comprise preferably only primary amino groups because the residues $C_2$ mainly serve for the introduction of additional hard segments without instable urea moieties into the inventive TPUUs in order to be able to better control the physical properties of the polyadducts.

However, in preferred embodiments, the residues $C_2$ also serve to provide biological degradability of the polyadducts or to improve them—depending on whether one or more of the residues I, M and $C_1$ comprise cleavable ester moieties. In particular when this is not the case, e.g., when M is derived from a polyether diol, preferred embodiments of the TPUUs of the present invention are characterized by the fact that at least one of the residues $C_2$ comprises one or more such ester moieties. Here, the residues $C_2$ are particularly preferably each independently derived from a diol selected from the following group: bis(hydroxyethyl) terephthalate, 1,4-butanediol, bis(3-hydroxypropyl) carbonate, 2-hydroxyethyl lactate, neopentyl glycol hydroxypivalate, 2-hydroxyethyl glycolate, because they have relatively short chains, are physiologically acceptable, are commercially available at low prices and are easy to handle.

In particularly preferred embodiments, a TPUU of the present invention is characterized by the fact that b+1=a+c and that the polyadduct corresponds to the following formula (IV):

$$-[(I-M-I-C_1)_a-(I-M-I-C_2)_c]_n- \quad (IV)$$

wherein a and c are each independently selected from 1 to 3, or a and c are each 1; and n≥5 or n≥10 or n≥20.

Thus, inventive TPUUs can be produced by a polyaddition method that can be easily controlled. According to the invention, the desired macrodiol (or various different ones) in a solution in a suitable anhydrous solvent is preferably first reacted with a bit more than the double amount of diisocyanate in order to obtain prepolymers, or intermediates, terminated with isocyanate on both sides, with the chain structure I-M-I, whereafter the two reactants introducing the chain extenders $C_1$ and $C_2$ are successively added in molar amounts, the sum of which corresponds to the molar amount of the macrodiol.

Due to the lower reactivity of sterically hindered amines and the instability of the urea compounds formed by them, in particular in solutions, the chain extender moiety $C_1$ is preferably introduced into the inventive TPUUs as last building block. Thus, the iso-cyanate-terminated prepolymer with the chain structure I-M-I is, in preferred embodiments, first reacted with the diol, diamine or amino alcohol containing $C_2$, which, for example, results in isocyanate-terminated intermediates with the chain structure I-M-I—$C_2$—I-M-I in case of a reaction of half the molar amount of chain extender with reference to the macrodiol units M. These are subsequently reacted with the chain extender rea-gent containing $C_1$, i.e., the diamine or amino alcohol containing sterically hindered amino groups, which, in case of equimolar amounts of the two chain extenders, results in a TPUU polymer with blocks of the structure of Formula (V):

$$-[I-M-I-C_1-I-M-I-C_2]_n- \quad (V)$$

i.e., TPUUs of Formula (I), wherein a=b=c=1. Here, the value of n, i.e., the number of blocks, and thus the chain length and the molecular weight of the TPUUs depend, in addition to the purity of the monomers as mentioned before, mainly on their stoichiometry as well as on the reaction sequence and here mainly on the order in which the various monomer or prepolymer components are added. Preferably is n≥5, more preferably ≥10, more preferably ≥20.

The above reaction sequence beginning with the production of intermediates terminated with isocyanates on both sides and having the chain structure I-M-I, followed by successive reactions with the two chain extender components is preferred according to the present invention, however, the latter is not limited thereto. For example, a mixture of the two chain extender components can be reacted with an amount of diisocyanates corresponding to (or slightly exceeding) the sum of the two molar amounts to produce a prepolymer in which only chain extender building blocks $C_1$ and $C_2$ are linked via diisocyanate building blocks I and are arranged alternatingly. These may then be reacted with macrodiol and further diisocyanate to the desired TPUU chains.

In this case, however, when using primary amines for introducing the $C_2$ units, initially, mainly the units $C_2$ would be linked via a diisocyanate due to the relative inertness of the sterically hindered amine compared to primary amines, before the majority of the $C_1$ units is incorporated into the chains, so that the latter are statistically more often found at the ends of prepolymer chains. This is, however, not preferred because this strategy leads to an accumulation of sterically hindered urea moieties at some positions of the final TPUU chains, namely at the ends of the hard segments containing the chain extenders, which would not improve the effect of the present invention and therefore be uneconomical. In addition, such polymer chains, which furthermore have relatively low molecular weights, i.e., low values of n, hardly show any increase of inter-molecular bonds within the polymer chains during subsequent water treatment due to the creation of hydrogen bridges by newly formed, not sterically hindered urea moieties. Compared to alcohols, sterically hindered amines are, however, more reactive. Consequently, diols are used for introducing $C_2$ units if these are, optionally at increased temperatures and/or by using catalysts, incorporated first into prepolymer chains before these are reacted with sterically hindered amines to yield the final TPUU chains because otherwise there would be undesired accumulations of sterically hindered urea moieties within hard segments or sometimes even incomplete incorporation of the $C_2$ units.

For these reasons, the above reaction sequence, beginning with the production of intermediates terminated on both sides with isocyanates and having the structure I-M-I and followed by separate reactions with the two chain extender components, is to be preferred according to the present invention. Furthermore, TPUUs are preferred that correspond to the above Formula (IV) and in particular Formula (V) because in these cases, the distances between the chain extender units $C_1$ and $C_2$ can easily be controlled by means of the length of the macrodiol.

The organic solvent used for producing the TPUUs is only limited insofar as it has to be anhydrous, i.e., absolute, inert towards the polyaddition reaction, i.e., aprotic, and be able to dissolve the monomers and the prepolymers formed therefrom as well as preferably also the desired polymers in order to enable high molecular weights of the latter, for which purpose it may also be heated, if necessary. Appropriate examples comprise aprotic polar solvents such as acetone, acetonitrile, tetrahydrofuran (THF), dimethylformamide (DMF), dimethyl sulfoxide (DMSO), N-methylpyrrolidone (NMP), and mixtures thereof. The temperatures for all partial reactions of the polyaddition are also not particularly limited, also depend on the reactivity of the monomers, and range from room temperature to the reflux temperature of the respective solvent. Preferred temperature ranges are, for example, 25-120° C., 40-80° C. or 50-70° C.

Due to the reactivity of the inventive TPUUs with water, the reaction system has to be kept anhydrous during the entire polyaddition, which includes, in addition to the use of absolute solvents, for example also the application of the well-known Schlenk line and/or other measures for excluding air humidity well-known to the skilled person.

The purification of the TPUUs can be carried out in a known and common way, for example by simple precipitation from the reaction solution, sometimes followed by a reprecipitation from the same or another solvent. For persons skilled in the art of polymer chemistry, appropriate procedures are part of their standard repertoire.

In a second aspect, the invention also relates to the use of the thermoplastic poly(urethane-urea) polyadducts as polymers self-reinforcing on contact with water in thermomechanical or solvent-based processing methods, where they are preferably processed to a solid product that is exposed to water or an aqueous environment during or after processing in order to improve one or more of its thermomechanical properties. Examples for such processing methods include all those mentioned at the beginning, including foil drawing and other thermal and solvent-based manufacturing processes.

Solid products obtained from the inventive TPUUs in this way, in particular from those with ester groups cleavable under physiological conditions and/or those with residues I, M, $C_1$ and $C_2$ as well as any cleavage products thereof that are physiologically acceptable, are preferably usable as biomaterial in biomedical applications where biological degradability is a great advantage. In particularly preferred embodiments of the invention, the thermoplastic poly(urethane-urea) polyadduct is therefore used for producing temporary body implants or the solid product obtained therefrom is usable as a temporary body implant.

Here, improvement of the thermomechanical as well as other properties of the inventive TPUUs can be achieved before or after implantation. For example, the TPUU material can, by means of one of the methods mentioned herein—or another method where improved properties are advantageous, be processed to a solid product that is to be used as body implant and is exposed to an aqueous environment for a certain period of time before implantation in order to effect "recombination reactions" analog to the above Scheme D. Or the solid product is implanted into the body of a patient in the state obtained during processing, whereafter it undergoes the reactions mentioned above and the concurrent improvement of properties due to the aqueous environment under physiological conditions. In both cases, it also undergoes cleavage of the ester bonds contained in the inventive TPUUs during its presence in the body, so that the polymer chains are gradually, e.g., over a period of several months or years, completely degraded.

SHORT DESCRIPTION OF THE DRAWINGS

Below, the present invention will be described in more detail by means of illustrative, non-limiting exemplary embodiments and with reference to the accompanying drawings, showing the following:

EXAMPLES

Figure 1:
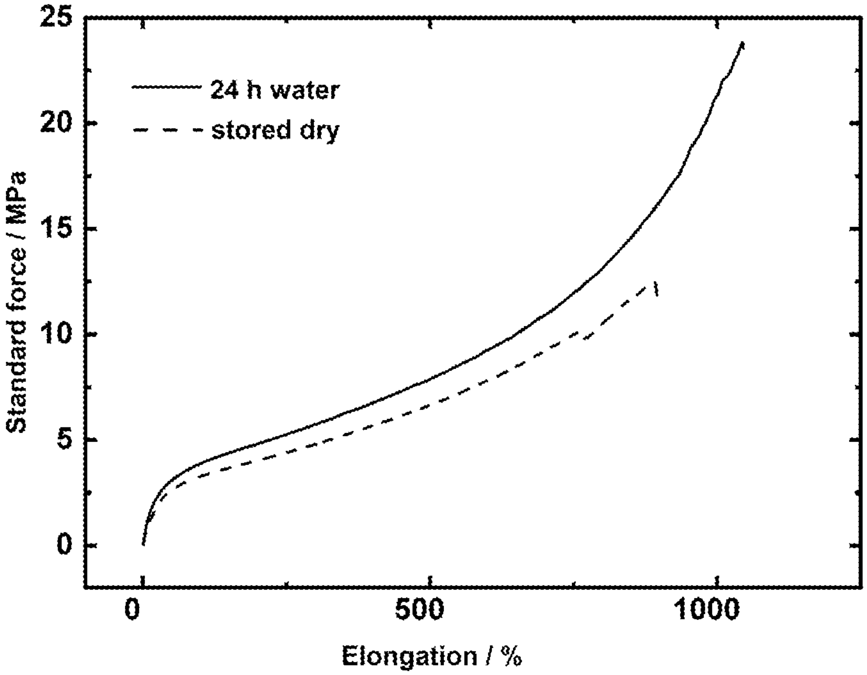
FIG. 1 shows a graphic comparison of the tensile elongations of foils drawn from TPUU produced in Example 1 after 24 hours of storage in a dry state and in water.

As representative examples for especially preferred embodiments of the present invention, multiple TPUUs were prepared using the beforementioned preferred reactive process, i.e. by sequentially reacting the individual components while initially preparing prepolymers or intermediates, respectively, with isocyanates on both sides having the chain structure I-M-I, which were sequentially reacted with both the reactants introducing the chain extenders $C_2$ and subsequently $C_1$. The reactants were used in varying molar ratios, wherein each sum of the molar quantities corresponded to the molar quantity of macrodiol.

In this way, multiple preferred TPUUs of the invention of Formula (I) were obtained:

$$—[I—M—(I—C_1)_a—(I—M)_b—(I—C_2)_c]_n— \quad (I)$$

wherein b+1=a+c, more specifically TPUUs of Formula (IV):

$$—[(I—M—I—C_1)_a—(I—M—I—C_2)_c]_n— \quad (IV)$$

wherein a and c are each selected from 1 and 3, and wherein $n \geq 10$ or $n \geq 20$.

Example 1

By using the standard Schlenk line with argon as the inert gas, first, pre-dried poly-(tetrahydrofuran) (pTHF) ($M_n \approx 1$ kDa, 6.059 g, 6.1 mmol, 1.00 eq., 19 ppm $H_2O$) as the macrodiol was weighed into a reaction flask and dried at 60° C. under high vacuum for 1 hour. Subsequently, 5 ml abs. dimethylformamide (DMF), followed by hexamethylene diisocyanate (HMDI) (2.111 g, 12.6 mmol, 2.07 eq.) in 5 ml abs. DMF were added to the dried, melted pTHF. After adding 2 drops (about 0.04 ml) of tin(II) 2-ethyl-hexanoate as a catalyst, the reaction mixture was magnetically stirred at 60° C. under protective argon atmosphere for 3 hours. Then, bis(hydroxyethyl) terephthalate (BHET) (0.770 g, 3.03 mmol, 0.5 eq.) was added as the diol for introducing $C_2$ as a solution in 5 ml abs. DMF. After further stirring at 60° C. for 3 hours, the reaction mixture was cooled to room temperature, after which N,N'-di-tert-butylethylenediamine (TBEDA) (0.522 g, 3.03 mmol, 0.5 eq.) was added as a secondary diamine for introducing $C_1$ that was sterically hindered on both sides. After each addition, the transfer vessels or syringes, respectively, were each flushed with 5 ml abs. DMF. The reaction solution was stirred overnight. To recover and purify the prepared TPUU, the reaction mixture was diluted with DMF and added dropwise to ten times the volume of diethyl ether, whereby a colorless precipitate was precipitated which was subsequently dried.

By reacting these reactants at a ratio of $C_1$:$C_2$:M:I=1:1:2:4 (or 4.14, respectively), an especially preferred TPUU of the invention of Formula (IV) above was obtained, wherein a=b=c=1, i.e. a TPUU of Formula (V):

$$—[I—M—I—C_1—I—M—I—C_2]_n— \quad (V)$$

The value n was calculated from the weight average molecular weight ($M_w$), as determined using gel permeation chromatography (GPC), and the molar mass of the blocks. The $M_w$ of the obtained TPUU was determined to be about 65.6 kDa, and the molar mass of one block was about 3.1 kDa, resulting in a value for the number of blocks n of about 21.

The precise structure of this TPUU of Formula (V) obtained in Example 1 is depicted overleaf. The average value m of the units M of polyTHF with a number average molecular weight $M_n$ of about 1 kDa is thus about 14.

Furthermore, the portions corresponding to the units $C_1$, $C_2$, M and I as well as their detailed structures are depicted below, wherein each bond denoted by an asterisk indicates the attachment to the carbonyl group of the urethane moieties or the urea moieties, respectively, that connect the individual units.

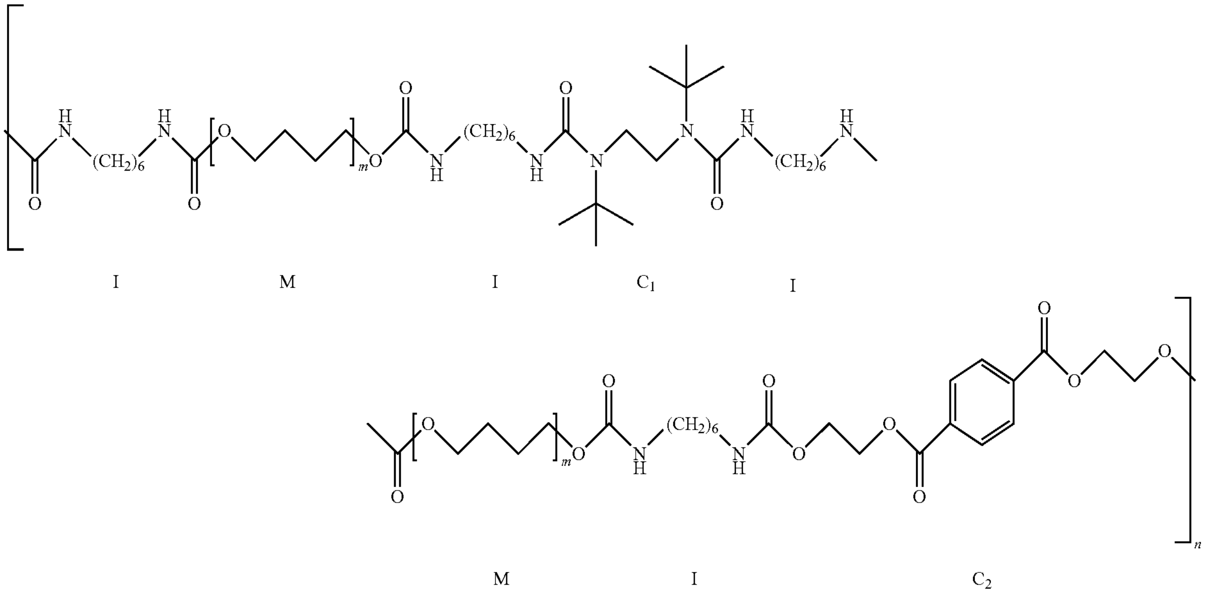

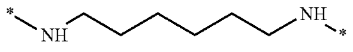

I

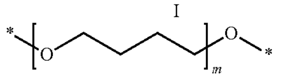

M

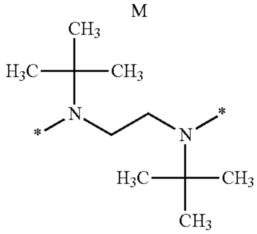

$C_1$

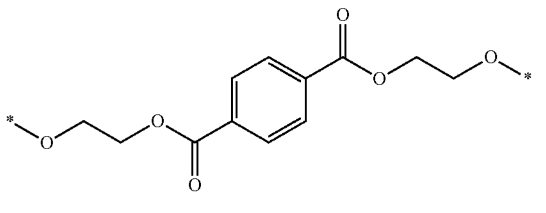

$C_2$

Example 2

To prepare another embodiment of the TPUUs of the invention, Example 1 was substantially repeated, wherein the molar ratio of the chain extender units $C_2$ and $C_1$ that were sequentially incorporated into the polymer chains was changed from 1:1 to 3:1. That is, at first, instead of 0.5 equivalents bis(hydroxyethyl) terephthalate 0.75 equivalents were reacted, and then instead of 0.5 equivalents N,N'-di-tert-butylethylenediamine only 0.25 equivalents were reacted.

By reacting the four reactants at a ratio of $C_1$:$C_2$:M:I=0.5:1.5:2:4 (or 4.14, respectively), a TPUU of Formula (IV) was obtained:

$$—[(I—M—I—C_1)_a—(I—M—I—C_2)_c]_n— \quad (IV)$$

wherein a=1 and c=3. The four portions that each contain one of the two chain extenders are randomly distributed within a block.

Using GPC, the $M_w$ of the TPUU thus obtained was determined to be about 62.8 kDa, and the molar mass of a block was about 6.3 kDa, resulting in a value for the number of blocks n of about 10.

Example 3

To prepare another preferred embodiment of a TPUU of the invention, Example 2 was substantially repeated, wherein in this case, the molar ratio between $C_2$ and $C_1$ was reversed. That is, at first, instead of 0.5 equivalents bis (hydroxyethyl) terephthalate only 0.25 equivalents were reacted, and then instead of 0.5 equivalents N,N'-di-tert-butylethylenediamine 0.75 equivalents were reacted.

By reacting the four reactants at a ratio of $C_1$:$C_2$:M:I=1.5:0.5:2:4 (or 4.14, respectively) a TPUU of Formula (IV) was obtained:

$$—[(I—M—I—C_1)_a—(I—M—I—C_2)_c]_n— \quad \text{(IV)}$$

wherein a=3 and c=1, and the four portions containing the chain extenders are randomly distributed within a block.

Using GPC, the $M_w$ of the TPUU thus obtained was determined to be about 74.4 kDa, and the molar mass of a block was about 6.1 kDa, resulting in a value for the number of blocks n of about 12.

In the following examples 4 to 13, by reacting the reactants anew at a ratio of $C_1$:$C_2$:M:I=1:1:2:4, similarly to the abovementioned Example 1—but by varying the components—other especially preferred TPUUs of the invention of Formula (V) were obtained, wherein a=b=c=1, i.e. TPUUs of Formula (V):

$$—[I—M—I—C_1—I—M—I—C_2]_n— \quad \text{(V)}$$

Example 4

Example 1 was substantially repeated, wherein instead of poly(tetrahydrofuran) (pTHF) ($M_n$≈1 kDa) as the macrodiol a poly(hexamethylene carbonate)diol (pHMC) having a number average molecular weight $M_n$ of about 1.2 kDa in abs. DMF was reacted with HMDI, BHET, and finally TBEDA as the secondary diamine sterically hindered on both sides, wherein by precipitating with diethyl ether the desired polyadduct was obtained as a flaky, colorless precipitate that was removed by filtration and dried.

Consequently, the structure of this TPUU corresponds to the depicted structure for the TPUU of Example 1 of Formula (V) —[I-M-I—$C_1$—I-M-I—$C_2$]$_n$— above, wherein the macrodiol radical derived from pTHF is replaced by the corresponding radical M derived from pHMC of the formula below, wherein the value for m is about 9.

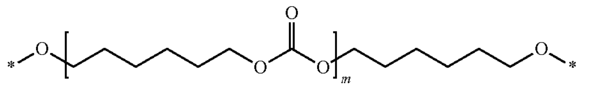

M

Using GPC, the $M_w$ of the TPUU thus obtained was determined to be about 128 kDa, and the molar mass of a block was about 3.6 kDa, resulting in a value for the number of blocks n of about 36.

Example 5

Example 1 was substantially repeated, wherein instead of poly(tetrahydrofuran) (pTHF) as the macrodiol a poly (caprolactone) diol, more precisely poly(caprolactone) diol-540 (pCL540) having a number average molecular weight $M_n$ of about 540 Da was reacted with HMDI, BHET, and finally TBEDA as the secondary diamine sterically hindered on both sides, wherein by precipitating with diethyl ether the desired polyadduct was obtained as a flaky, colorless precipitate that was removed by filtration and dried.

Consequently, the structure of this TPUU corresponds to the depicted structure for the TPUU of Example 1 of Formula (V) —[I-M-I—$C_1$—I-M-I—$C_2$]$_n$— above, wherein the macrodiol radical derived from pTHF is replaced by the corresponding radical M derived from pCL540 of the formula below, wherein the value for each m≈2.

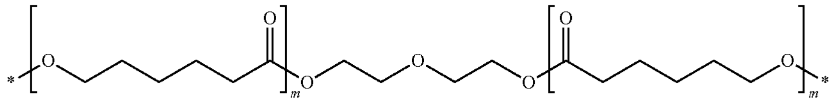

M

Using GPC, the $M_w$ of the TPUU thus obtained was determined to be about 62.4 kDa, and the molar mass of a block was about 2.2 kDa, resulting in a value for the number of blocks n of about 28.

Example 6

Example 5 was substantially repeated, wherein instead of poly(tetrahydrofuran) (pTHF) as the macrodiol, again, a poly(caprolactone) diol, but in this case poly-(caprolactone) diol-2000 (pCL2000) having a number average molecular weight $M_n$ of about 2.2 kDa was reacted with HMDI, BHET, and TBEDA, wherein by precipitating with diethyl ether the desired polyadduct was obtained as a sticky, colorless precipitate that was removed from the reaction vessel with a spatula and dried.

The structure of this TPUU corresponds to that of the TPUU of Example 5, but having accordingly higher values for the degree of polymerization m of the radical M derived from pCL2000, namely about 9 each.

Using GPC, the $M_w$ of the TPUU thus obtained was determined to be about 56.4 kDa, and the molar mass of a block was about 5.4 kDa, resulting in a value for the number of blocks n of about 10.

Example 7

Example 4 was substantially repeated, wherein instead of hexamethylene diisocyanate (HMDI) 4,4'-diisocyanato dicyclohexylmethane (H12MDI) as the diisocyanate was reacted with pHMC, BHET, and finally TBEDA as the secondary diamine sterically hindered on both sides, wherein by precipitating with diethyl ether the desired polyadduct was obtained as a flaky, colorless precipitate that was removed by filtration and dried.

Consequently, the structure of this TPUU corresponds to the depicted structure for the TPUU of Example 1 of Formula (V) —[I-M-I—$C_1$—I-M-I—$C_2$]$_n$— above, wherein radical M derived from pTHF is replaced by radical M derived from pHMC (m=9) and radical I derived from HMDI is replaced by radical I derived from H12MDI of the following formulae.

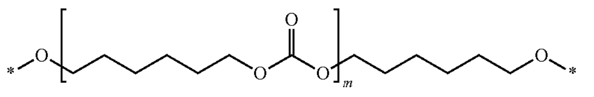

M

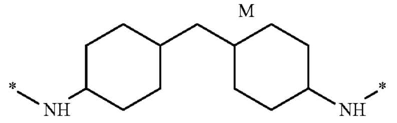

I

Using GPC, the $M_w$ of the TPUU thus obtained was determined to be about 46.2 kDa, and the molar mass of a block was about 3.5 kDa, resulting in a value for the number of blocks n of about 13.

Example 8

Example 1 was substantially repeated, wherein instead of bis(hydroxyethyl) terephthalate (BHET) 1,4-butanediol (BDO) as the chain extender for introducing $C_2$ was reacted with pTHF, HMDI, and TBEDA as the secondary diamine sterically hindered on both sides, wherein by precipitating with diethyl ether the desired polyadduct was obtained as a sticky, colorless precipitate that was removed from the reaction vessel with a spatula and dried.

Consequently, the structure of this TPUU corresponds to the depicted structure for the TPUU of Example 1 of Formula (V) —[I-M-I—$C_1$—I-M-I—$C_2$]$_n$— above, wherein the radical derived from BHET is replaced by the radical $C_2$ derived from BDO of the following formula.

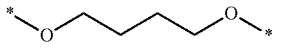

$C_2$

Using GPC, the $M_w$ of the TPUU thus obtained was determined to be about 54.7 kDa, and the molar mass of a block was about 3.0 kDa, resulting in a value for the number of blocks n of about 18.

Example 9

Example 1 was substantially repeated, wherein instead of BHET bis(3-hydroxypropyl) carbonate (BHPC) as the chain extender for introducing $C_2$ was reacted with pTHF, HMDI, and TBEDA as the secondary diamine sterically hindered on both sides, wherein by precipitating with diethyl ether the desired polyadduct was obtained as a sticky, colorless precipitate that was removed from the reaction vessel with a spatula and dried.

Consequently, the structure of this TPUU corresponds to the depicted structure for the TPUU of Example 1 of Formula (V) —[I-M-I—$C_1$—I-M-I—$C_2$]$_n$— above, wherein the radical derived from BHET is replaced by the corresponding radical $C_2$ derived from BHPC of the following formula.

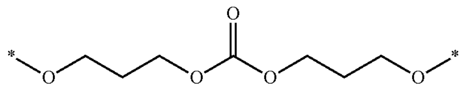

$C_2$

Using GPC, the $M_w$ of the TPUU thus obtained was determined to be about 163 kDa, and the molar mass of a block was about 3.1 kDa, resulting in a value for the number of blocks n of about 53.

Example 10

Example 1 was substantially repeated, wherein instead of BHET 2-hydroxyethyl lactate (ethylene glycol lactate, EGLA) as the chain extender for introducing $C_2$ was reacted with pTHF, HMDI, and TBEDA as the secondary diamine sterically hindered on both sides, wherein by precipitating with diethyl ether the desired polyadduct was obtained as a sticky, colorless precipitate that was removed from the reaction vessel with a spatula and dried.

Consequently, the structure of this TPUU corresponds to the depicted structure for the TPUU of Example 1 of Formula (V) —[I-M-I—$C_1$—I-M-I—$C_2$]$_n$—above, wherein the radical derived from BHET is replaced by the corresponding radical $C_2$ derived from EGLA of the following formula.

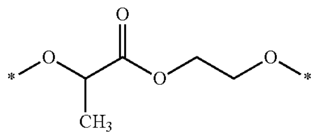

$C_2$

Using GPC, the $M_w$ of the TPUU thus obtained was determined to be about 58.9 kDa, and the molar mass of a block was about 3.0 kDa, resulting in a value for the number of blocks n of about 19.

Example 11

Example 1 was substantially repeated, wherein instead of N,N'-di-tert-butylethylenediamine (TBEDA) N-tert-butylaminoethanol (TBAE) as the chain extender for introducing $C_1$, i.e. an amino alcohol with only one sterically hindered secondary amino group, was reacted with pTHF, HMDI, and BHET, wherein by precipitating with diethyl ether the desired polyadduct was obtained as a flaky, colorless precipitate that was removed by filtration and dried.

Consequently, the structure of this TPUU corresponds to the depicted structure for the TPUU of Example 1 of Formula (V) —[I-M-I—$C_1$—I-M-I—$C_2$]$_n$— above, wherein the radical derived from TBEDA is replaced by the corresponding radical $C_1$ derived from TBAE of the following formula.

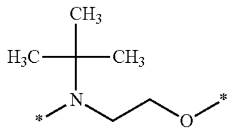

$C_1$

Using GPC, the $M_w$ of the TPUU thus obtained was determined to be about 103 kDa, and the molar mass of a block was about 3.1 kDa, resulting in a value for the number of blocks n of about 33.

Example 12

Example 1 was substantially repeated, wherein instead of N,N'-di-tert-butylethylenediamine (TBEDA) N,N'-diisopropylethylenediamine (IPEDA) as a chain extender for introducing $C_1$, i.e. a diamine with a slightly weaker sterically hindered secondary amino group, was reacted with pTHF, HMDI, and BHET, wherein by precipitating with diethyl ether the desired polyadduct was obtained as a flaky colorless precipitate that was removed by filtration and dried.

Consequently, the structure of this TPUU corresponds to the depicted structure for the TPUU of Example 1 of Formula (V) —[I-M-I—$C_1$—I-M-I—$C_2$]$_n$—above, wherein the radical derived from TBEDA is replaced by the corresponding radical $C_1$ derived from IPEDA of the following formula.

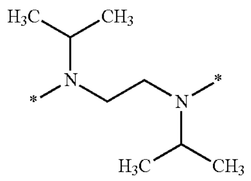

$C_1$

Using GPC, the $M_w$ of the TPUU thus obtained was determined to be about 85.3 kDa, and the molar mass of a block was about 3.1 kDa, resulting in a value for the number of blocks n of about 28.

Example 13

Example 1 was substantially repeated, wherein instead of N,N'-di-tert-butylethylenediamine (TBEDA) 2,6-dimethylpiperazine (2,6-DMP) as a chain extender for introducing $C_1$, i.e. a cyclic diamine with only one sterically hindered secondary amino group (the second amino group is also secondary, but not sterically hindered according to the invention as shown in Example 14 for Comparison Example 3) was reacted with pTHF, HMDI, and BHET, wherein by precipitating with diethyl ether the desired polyadduct was obtained as a solid, colorless precipitate that was removed by filtration and dried.

Consequently, the structure of this TPUU corresponds to the depicted structure for the TPUU of Example 1 of Formula (V) —[I-M-I—$C_1$—I-M-I—$C_2$]$_n$—above, wherein the radical derived from TBEDA is replaced by the corresponding radical $C_1$ derived from 2,6-DMP of the following formula.

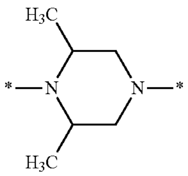

$C_1$

Using GPC, the $M_w$ of the TPUU thus obtained was determined to be about 153.4 kDa, and the molar mass of a block was about 3.1 kDa, resulting in a value for the number of blocks n of about 49.

Comparison Example 1

Similarly to Example 1, a comparison polymer was prepared by reacting pTHF, HMDI, and BHET, wherein no sterically hindered secondary diamine for introducing $C_1$ was added, but an amount of BHET equimolar to the amount of pTHF was used. As a result, the ratio of radicals in the polyadduct was $C_2$:M:I=1:1:2, which is thus a thermoplastic poly(urethane) (TPU; without urea moieties) of the following Formula (VI):

$$—[I—M—I—C_2]_n— \quad (VI)$$

Using GPC, the $M_w$ of the TPUU thus obtained was determined to be 46 kDa, and the molar mass of a block was about 1.6 kDa, resulting in a value n of about 29.

Due to the cleavable ester bonds in $C_2$, this TPU is degradable under physiological conditions, but, does not have any self-enhancing properties.

Comparison Example 2

To compare the TPUUs above with a commercially available TPU, a thermoplastic poly(urethane) without urea moieties, Pellethane® 2363-80A was acquired from Lubrizol LifeSciences. This is a non-biodegradable TPU made from methylene di(phenyl-isocyanate) (MDI), poly(tetrahydrofuran) (pTHF) and 1,4-butanediol, having a molecular weight $M_n$ of about 37 kDa and a $M_w$ of about 63 kDa which was subjected to the same tests as the polyadducts of the Examples of the invention and the other Comparison Examples.

Comparison Example 3

Example 1 was substantially repeated, wherein instead of N,N'-di-tert-butylethylenediamine (TBEDA), piperazine (Pip) as the chain extender for introducing $C_1$, i.e. a cyclic diamine with two secondary amino groups, but not sterically hindered according to the invention, as shown in Example 14, was reacted with pTHF, HMDI, and BHET, wherein by precipitating with diethyl ether the desired polyadduct was obtained as a solid, colorless precipitate that was removed by filtration and dried.

Consequently, the structure of this TPUU corresponds to the depicted structure for the TPUU of Example 1 of Formula (V) —[I-M-I—$C_1$—I-M-I—$C_2$]$_n$— above, wherein the radical derived from TBEDA is replaced by the corresponding radical $C_1$ derived from Pip of the following formula.

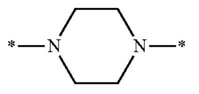

$C_1$

Using GPC, the $M_w$ of the TPUU thus obtained was determined to be about 325.5 kDa, and the molar mass of a block was about 3.1 kDa, resulting in a value for the number of blocks n of about 105.

Comparison Example 4

Example 1 was substantially repeated, wherein instead of N,N'-di-tert-butylethylenediamine (TBEDA), 2,5-dimethylpiperazine (2,5-DMP) as the chain extender for introducing $C_1$, i.e. again a cyclic diamine with two secondary amino groups, neither of which sterically hindered according to the invention, as shown in Example 14, was reacted with pTHF, HMDI, and BHET, wherein by precipitating with diethyl ether the desired polyadduct was obtained as a solid, colorless precipitate that was removed by filtration and dried.

Consequently, the structure of this TPUU corresponds to the depicted structure for the TPUU of Example 1 of Formula (V) —[I-M-I—$C_1$—I-M-I—$C_2$]$_n$—above, wherein the radical derived from TBEDA is replaced by the corresponding radical $C_1$ derived from 2,5-DMP of the following formula.

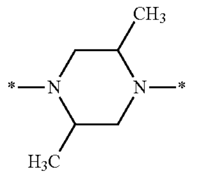

$C_1$

Using GPC, the $M_w$ of the TPUU thus obtained was determined to be about 51.8 kDa, and the molar mass of a block was about 3.1 kDa, resulting in a value for the number of blocks n of about 17.

Example 14

Foil Preparation and Testing

The TPUUs of the invention obtained in Examples 1 to 13 and the TPUs of Comparison Examples 1 to 4 were dissolved in abs. DMF at a concentration of 10% by weight. These solutions were poured into Teflon molds, sized 60×40×2 mm, and the solvent was removed by evaporation at room temperature. After 24 h, the foils thus obtained were dried for further 3 d in the desiccator under vacuum, after which their thickness was measured using an electronic external measuring gauge K110T from Kroeplin which was about 100 μm in every case. Then one half of the foils was immersed in deionized water and, like the other half that was left in a dry state, stored for up to 28 d at room temperature. Before conducting any tests, any wet-stored samples were dried in a desiccator at 80° C. and 120 mbar for 24 h.

Tensile Testing

After dry or wet storage (and drying) of the foils, respectively, for the indicated duration of time, three parts of the TPUU foils each were die-cut as type 5B tensile testing samples and subjected to tensile testing according to ISO 527-1 using a Zwick Z050 tensile tester, wherein the samples that had been chucked in the tensile tester were pulled apart at a speed of 50 mm/min until they broke. Each sample was tested in triplicate, the results were averaged, and the thus measured elongation at break (as a percentage of the initial length) was used as a measure for the foil tear strength and the ultimate tensile strength (in MPa) as a measure for tensile strength. Table 1 below shows direct comparisons of the mean values thus obtained for every time as difference between mean values that were calculated for the wet-stored samples and the dry-stored samples, $\Delta_{wet-dry}$, each indicated as a percentage of the value for the dry sample.

Furthermore, FIG. 1 graphically depicts the results of first tests after only 24 h of storage for the TPUU of Example 1. In this case, a comparison between each tolerated maxi-mum standard force between the dry and the wet samples serves as a measure for the self-enhancement of the TPUUs of the invention due to the abovementioned recombination reactions when contacted with water. It is apparent from FIG. 1 that the dry-stored foil broke at an elongation of about 800%, i.e. about 9 times its initial length, whereas the foil that had been stored for 24 h in water even withstood an elongation of over 1000%, i.e. 11 times its initial length.

Figure 2:
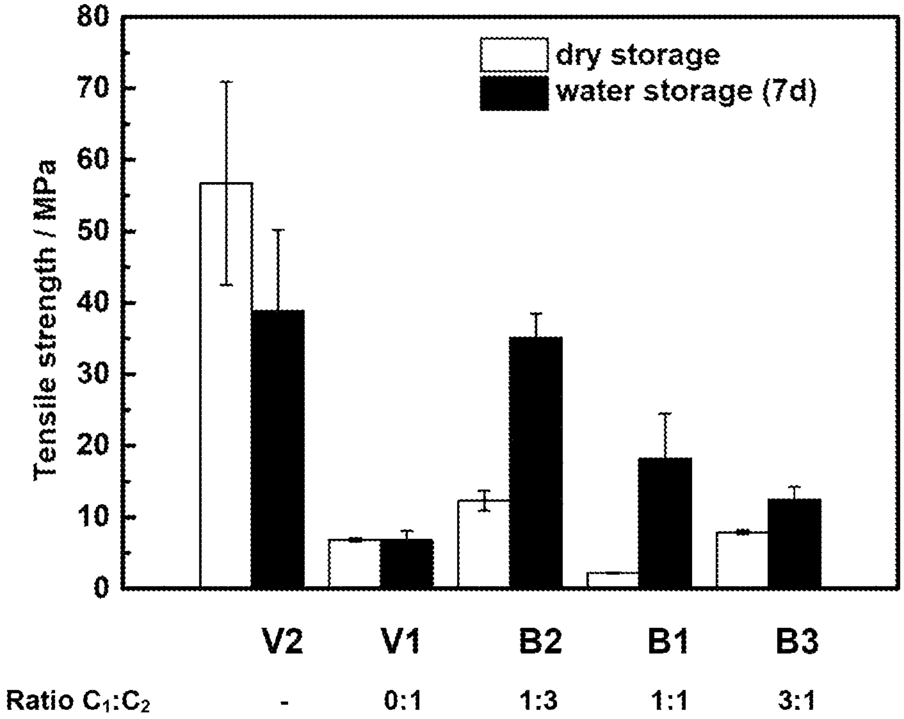
FIG. 2 shows a graphic comparison of the tensile strengths of foils drawn from TPUU produced in Examples 1 to 3 according to the present invention and from known TPUs after 7 hours of storage in a dry state and in water.

FIG. 2 graphically depicts the results (each averaged from triplicates) of tensile tests with a first series of foils of Examples 1 to 3 and Comparison Examples 1 and 2 that were dry or wet-stored (and dried), respectively, for 7 d. It is apparent that all three TPUUs of the invention experienced an enhancement of their tensile strength when stored in water. The TPUU of Example 2 that contained the smallest number of unstable urea compounds of the chain extender moieties $C_1$, and consequently, created new polymers with the greatest chain lengths through the recombination reactions when contacted with water (analogously to Scheme D) showed the strongest tensile strength, whereas the TPUUs of Examples 1 and 3 that contained twice or three times the amount of $C_1$ units, respectively, experienced a respective smaller degree of improvement. Nevertheless, even the TPUU of Example 3 having 3 times the amount of unstable urea compounds than that of Example 2 and therefore had had to experience the biggest amount of recombination reactions within the original polymer chain showed an improved tensile strength of about 50% compared to the corresponding dry-stored polymer.

In contrast, the TPU of Comparison Example 1 without unstable urea compounds had basically the same tensile strength after dry and wet storage, whereas the tensile strength of the TPU of Comparison Example 2 that was multiple times the one of the other tested polymers in a dry state had decreased by about a third when stored in water. While not wishing to be bound by theory, the inventors attribute this to the breaking of hydrogen bonds between urethane moieties of adjacent polymer chains due to swelling during the storage in an aqueous environment. As a result, the decreased tensile strength of the TPUs of Comparison Example 2 was in the range of the tensile strength of the TPUUs of the invention of Example 2 that was improved due to the wet storage.

After these first tests with TPUUs of the invention of Examples 1 to 3 and the TPUs of the Comparison Examples 1 and 2 those five polymers as well as TPUUs of Examples 4 to 13 and the Comparison Examples 3 and 4 were tested in a further test series. To this end, foil samples that had been wet-stored or dry-stored, respectively, for 24 h, 7 d and 28 d at room temperature were tested in triplicate.

Table 1 overleaf lists, as mentioned before, the differences of the mean values of the values that were measured for all samples of Examples 1 to 13 and the Comparison Examples 1 to 4 after their respective storage times (24 h, 7 d, or 28 d) at room temperature. Since, in most cases, the values that were determined after 7 d were already representative, only the value after 7 d was determined for some later Examples and Comparison Examples.

Due to the fact that the amount of sterical hindrance of the secondary diamines that were employed as chain extenders for introducing the radical $C_1$ was small to non-existent, those four TPUUs were subjected another test series at 60° C. to enhance their reactivity. The respective differences of the mean values after a storage time of 24 h as well as 7 d are indicated in Table 2 below.

TABLE 1

Results of tensile testing with three foils each, wet-stored or dry-stored, respectively, at room temperature

| Example | Tear strength, [%] $\Delta_{wet\text{-}dry}$ [%] | | | Tensile strength, [MPa] $\Delta_{wet\text{-}dry}$ [%] | | |
|---|---|---|---|---|---|---|
| | 24 h | 7 d | 28 d | 24 h | 7 d | 28 d |
| Example 1 | −6 | **30** | −14 | −3 | **67** | **30** |
| Example 2 | −4 | **10** | **43** | −1 | **48** | **17** |
| Example 3 | 4 | **1147** | **425** | 0 | **331** | **107** |
| Example 4 | −9 [1)] | −9 [1)] | 12 [1)] | 15 [1)] | **23** | **82** |
| Example 5 | **74** | **176** | **625** | **45** | **16** | **52** |
| Example 6 | −1 [1)] | 5 [1)] | **24** | **35** | **51** | **81** |
| Example 7 | −80 | −30 | −28 [1)] | **55** | **33** | 22 [1)] |
| Example 8 | **136** | **288** | **367** | **133** | **297** | **286** |
| Example 9 | **317** | **818** | **1688** | **38** | **75** | **552** |
| Example 10 | 0 [1)] | 0 | 44 [1)] | 0 [1)] | 0 [1)] | **32** |
| Example 11 | **226** | **306** | **548** | **105** | **85** | **103** |
| Example 12 | −14 [1)] | −1 [1)] | 1 [1)] | 0 [1)] | 11 [1)] | 4 [1)] |
| Example 13 | | −4 | | | **54** | |
| Comparison Example 1 | −1 [1)] | 22 [1)] | 9 [1)] | 7 [1)] | −1 [1)] | 4 [1)] |
| Comparison Example 2 | −3 [1)] | 1 [1)] | 7 [1)] | 2 [1)] | 14 [1)] | 1 [1)] |
| Comparison Example 3 | | −7 [1)] | | | 10 [1)] | |
| Comparison Example 4 | | −5 [1)] | | | 9 [1)] | |

[1)] statistically not significant, since the standard deviations of the mean values overlap

TABLE 2

Results of tensile testing with three foils each, wet-stored or dry-stored, respectively, at 60° C.

| Example | Tear strength, [%] $\Delta_{wet\text{-}dry}$ [%] | | Tensile strength, [MPa] $\Delta_{wet\text{-}dry}$ [%] | |
|---|---|---|---|---|
| | 24 h | 7 d | 24 h | 7 d |
| Example 12 | 5 [1)] | 9 [1)] | 52 | 146 |
| Example 13 | −13 | | 76 | |
| Comparison Example 3 | −30 [1)] | −21 [1)] | −18 [1)] | −52 [1)] |
| Comparison Example 4 | 2 [1)] | −15 [1)] | 28 [1)] | 3 [1)] |

[1)] statistically not significant, since the standard deviations of the mean values overlap It is clear from Table 1 that for the Examples of the invention for the majority of the measured values a contact with water at room temperature led to an improvement of the tear strength or tensile strength, respectively, by a double-digit percentage range (highlighted in bold). In the Comparison Examples, this is only the case with three measured values which also show overlapping standard deviations of mean values and are therefore not statistically significant. Therefore, as expected, no significant change in mechanical properties after a wet storage was measurable in any samples of the Comparison Examples.

As a measure for "self-enhancement" of the solid samples prepared from the TPUUs of the invention due to recombination reactions when contacted with water, as shown in Scheme D (or for the chain extender only sterically hindered on one side of Example 11 in Scheme E, respectively), especially the tensile strength improvements are relevant. Here, six out of twelve examples of the invention already show an improvement in a double-digit percentage range after 24 h and even eleven out of thirteen examples after 7 d or 28 d of wet storage, respectively. Furthermore, for four examples all measured values were substantially improved after a wet storage compared to a dry storage, among them also Example 11 having only one unstable urea group per $C_1$ unit.

Consequently, the occurrence of the above mentioned recombination reactions was demonstrated for almost all examples of the present invention—representing various components of the TPUUs of the invention and different proportions of sterically hindered urea groups per molecule. The only exception being the TPUU of Example 12 with nitrogen atoms substituted with isopropyl that caused a relatively low sterical hindrance.

Therefore, the polymer of Example 12 as well as the TPUU of Example 13, using 2,6-dimethylpiperazine as the diamine sterically hindered on one side, together with both piperazine-containing TPUUs of Comparison Examples 3 and 4, i.e. with piperazine or 2,5-dimethylpiperazine, respectively, as $C_1$ units, were subjected to another test at 60° C., to determine whether the reactivity of the urea group could be increased with higher temperatures.

As apparent from Table 2, this was the case for both examples of the invention, especially since the tensile strength for the isopropyl-containing TPUU of Example 12 was already increased after 24 h by more than 50% and after 7 d by almost 150%. The 2,6-dimethylpiperazine-containing TPUU of Example 13 also showed an increased tensile strength by over 75% after already 24 h at 60° C. In contrast, the increase in temperature in the Comparison Examples 3 and 4 containing piperazine or 2,5-dimethylpiperazine, respectively, did not have the desired effect—on the contrary: in this case, the values at 60° C. were even worse than after storage at room temperature.

This dearly shows that the piperazine-containing or 2,5-dimethylpiperazine-containing TPUUs, respectively, from the literature cited in the beginning are not sterically hindered according to the invention, whereas TPUUs substituted with isopropyl certainly are.

Comparatively bad were also the results at room temperature for the TPUU of Example 7 in which the tear strength compared to dry storage even decreased and a clear improvement of the tensile strength after only 24 h weakened in the course of further wet storage, as well as for Example 10 in which a clear improvement was observed only after 28 d. While not wishing to be bound by theory, the inventors attribute this to the following circumstances.

The self-enhancing effect caused by the recombination reactions is not only influenced by the type and position of the unstable urea groups in the molecule, but also strongly by the structure of the polymer, i.e. the relative self-enhancement depends on the storage time as well as on the building blocks of the TPUU. Specifically, the stable urea groups formed by the recombination reactions result in a stiffening of the polymer matrix as a whole. At a certain concentration of these urea groups, this leads to the self-enhancing effect being "saturated". Consequently, sterically hindered, unstable urea groups that still exist at this point cannot undergo a recombination reaction according to the principle of Schemes D and E since the primary amines and isocyanates formed in situ in the matrix are no longer mobile enough to bond with each other. As a result, from this point on, they no longer serve as self-enhancing groups, but rather as degradable groups, as shown in Scheme F. Because of this, especially when stored in water for a longer period of time and/or in case of a high number of sterically hindered urea groups, the self-enhancing effect can be weakened or even turn into a degradation effect.

This effect is especially pronounced for the TPUU of Example 7 that has a very rigid matrix due to the presence of H12MDI and pHMC. Even though a pronounced self-enhancement was observed after only 24 h it had already decreased in test samples that were wet-stored for 7 d. After 28 d of wet storage no significant self-enhancing effect caused by newly formed stable urea groups was observed since it was compensated for by the degradation of still existing sterically hindered urea groups.

The reason why in Example 10 improvements could only be observed after 28 d could be attributed to the fact that a hydrolysis of part of the lactic acid ester bonds compensated for the self-enhancing effect achieved by recombination, i.e. again degradation reactions. When using the TPUUs of the invention as temporary body implants such a hydrolysis may be desirable, though.

In any case, this self-enhancement's dependence on the matrix stiffness induced by the remaining components (macrodiol, diisocyanate, chain extenders) and on simultaneously occurring degradation reactions shows that the ideal wet storage time for achieving the respective desired effect obviously varies for differently composed TPUUs.

Melting Point Determination

Furthermore, the melting points of the TPUUs of the invention contained in the foils of the TPUUs of Examples 1 to 3 from the first test series were determined using DSC. Table 3 below shows the values measured.

TABLE 3

| Example | Ratio $C_1$:$C_2$ | Tmax-dry (° C.) | Tmax-wet (° C.) | ΔT (° C.) |
|---|---|---|---|---|
| 1 | 1:1 | 80.41 | 85.81 | 5.40 |
| 2 | 1:3 | 87.44 | 92.26 | 4.82 |
| 3 | 3:1 | 75.38 | 84.41 | 9.03 |

These values show that an increase of the peak melting temperatures was observed for all polymers "recombined" by reaction with water, wherein the TPUU of Example 3 with the highest proportion of unstable urea compounds in $C_1$ had the lowest melting point, but experienced the greatest increase through the recombination reactions with water. Accordingly, the TPUU of Example 2 having the fewest $C_1$ units within the polymer chain showed the highest melting point that experienced the smallest increase due to the smallest number of recombination reactions in water.

Example 15

Degradability

To evaluate if the new polyadducts of the present invention are degradable under physiological conditions a foil was prepared from the TPUU prepared in Example 1 with a chain extender unit ratio of $C_1$:$C_2$=1:1 similarly to Example 12, but in this case with an average thickness of 800 μm. 15 circular disks with a diameter of 5 mm were die-cut form the foil, the weights of which were determined more precisely, but were each between 15 and 20 mg.

Then, to simulate physiological conditions, every disk was placed in a test tube in 20 ml PBS (1×, pH 7.4) after which the test tubes were heated in an autoclave to 90° C. After 7, 14, 25, 35, and 41 d three each were taken. The disks therein contained were placed in deionized water three times for 15 min to remove the contained salts. Subsequently, the drained net weight as well as—after drying to constant weight (24 h at 80° C. and 120 mbar) —the dry weight was determined, and a molecular weight determination using gel permeation chromatography was performed. From the values thus obtained loss of mass, decrease of molecular weight and swelling of the individual samples were calculated according to the equations 1 to 3 below.

$$m_{eros}(t) = \frac{m_t - m_0}{m_0} \cdot 100 \qquad \text{Equation 1}$$

$$\% \; \overline{M}_w(t) = \frac{\overline{M}_w(t)}{\overline{M}_w(0)} \cdot 100 \qquad \text{Equation 2}$$

$$s(t) = \frac{m_t^w - m_t}{m_t} \cdot 100 \qquad \text{Equation 3}$$

$m_{eros}(t)$ Loss of mass after t days of degradation t Degradation time in d $m_t$ Sample weight after t days of degradation in mg $m_0$ Sample weight before degradation in mg % $\overline{M}_w(t)$ Decrease of molecular weight after t days of degradation in %

$\overline{M}_w(t)$ Molecular weight after t days of degradation in kDa $\overline{M}_w(0)$ Molecular weight before degradation in kDa s(t) Swelling of sample after t days of degradation in %

$m_t^w$

Drained net weight of sample after t days of degradation in mg

Figure 3:
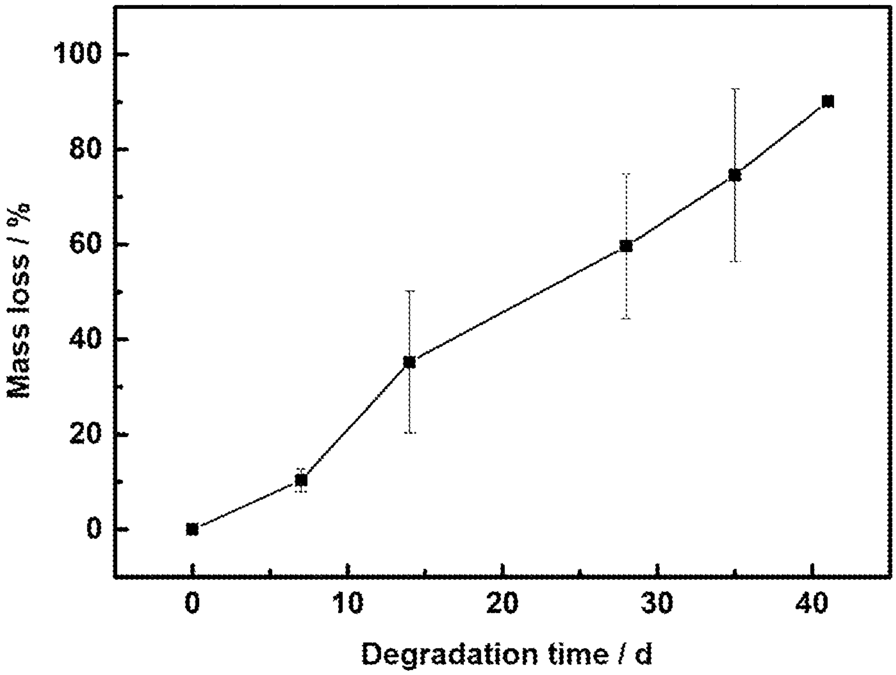
FIGS. 3 to 5 show the results of an experiment for examining degradability of the inventive TPUUs under simulated physiological conditions.
Figure 4:
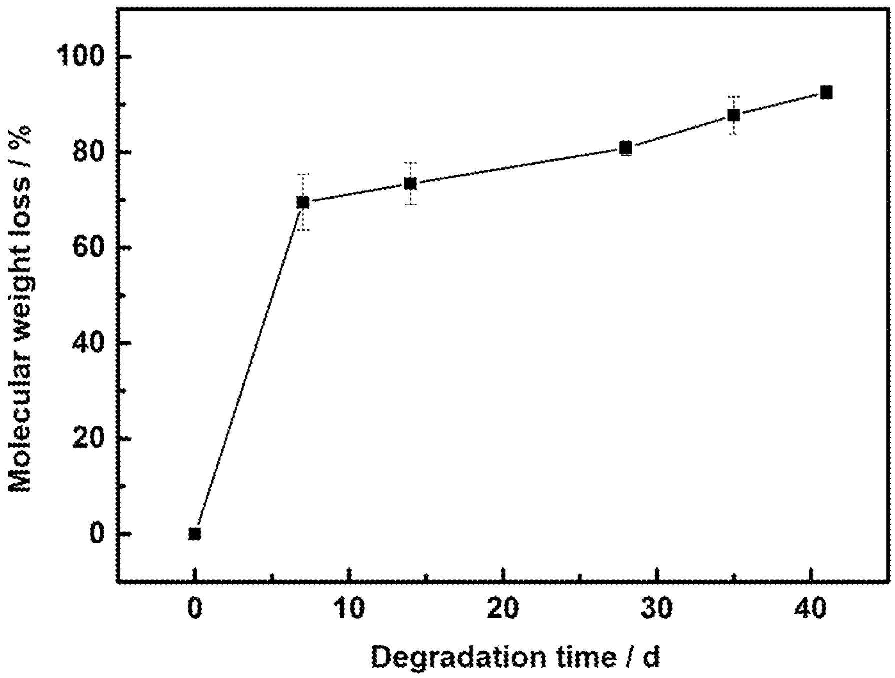
Figure 5:
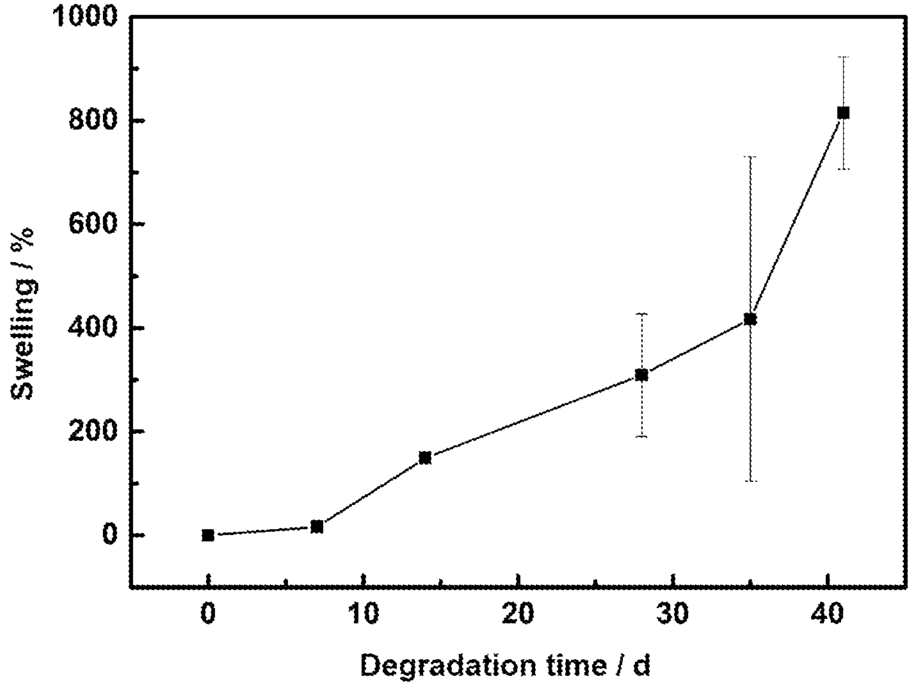

The results of these calculations are graphically illustrated in FIGS. 3 to 5. Primarily, they show that already after 7 d the molecular weight had decreased by about ¾ of the molecular initial weight—with about 10% loss of mass and barely increased swellability, and after 41 d, by the end of the degradation study, it had decreased by about 90%—just like the loss of mass. From an extrapolation of the graphs of FIGS. 3 and 4, it can be deducted that the degradation would have been complete after about another week at 90° C. in PBS, i.e. after about a total of 7 weeks.

By comparing the proportions of the chain extender units $C_1$ and $C_2$ of the TPUU of Example 1 tested in this example with those of both polyadducts of Examples 2 and 3 in which the proportion of cleavable ester moieties in $C_2$ is twice or half as high, respectively, it can be deducted that the TPUU of Example 2 would have degraded much faster and that of Example 3 much slower. Furthermore, it is expected that it should not make much of a difference if these cleavable ester moieties are contained in the units $C_2$ or in the isocyanate units I, in the macrodiol units M, or within the units $C_1$ derived from sterically hindered amines. Corresponding investigations are object of the current research of the inventors.

In summary, the explanations above show that the TPUUs of the present invention are completely degradable under simulated physiological conditions and that the rate of degradation can be controlled through the proportions of cleavable ester moieties.

Reference Examples 1 to 4—NMR Tests

NMR has been identified as a method for determining with less effort which secondary amines are sterically hindered amines according to the invention that, upon reaction with isocyanates, form unstable bonds with the carbonyl group of the resulting urea moieties. But since identifying individual signals in a polymer matrix using NMR with sufficient accuracy is not possible, multiple model molecules were synthesized according to Scheme G below, by reacting each secondary diamine $R_2$—NH—$R_1$—NH—$R_2$ on both sides with monofunctional hexyl isocyanate.

-continued

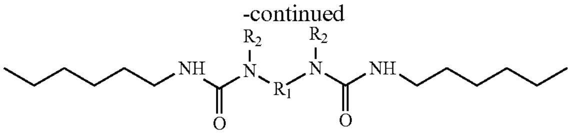

This results in two urea groups that would also be the part of the chain that is relevant for the self-enhancing effect in the TPUUs of the invention, but that can be examined in the model molecules without interfering signals by means of NMR.

The reactivity of these urea groups was tested in solution in deuterochloroform by adding propylamine. If they are sterically hindered, unstable urea compounds that open reversibly in solution while forming free amino groups and isocyanates and close when returning to their original urea group, it is possible for the intermediarily formed isocyanates to react with propylamine while forming one or two non sterically hindered and therefore stable urea groups; see Scheme H below. Since, in this way, new signals can be detected using NMR, a clear identification of the reactivity of each secondary amine can be made.

Scheme H

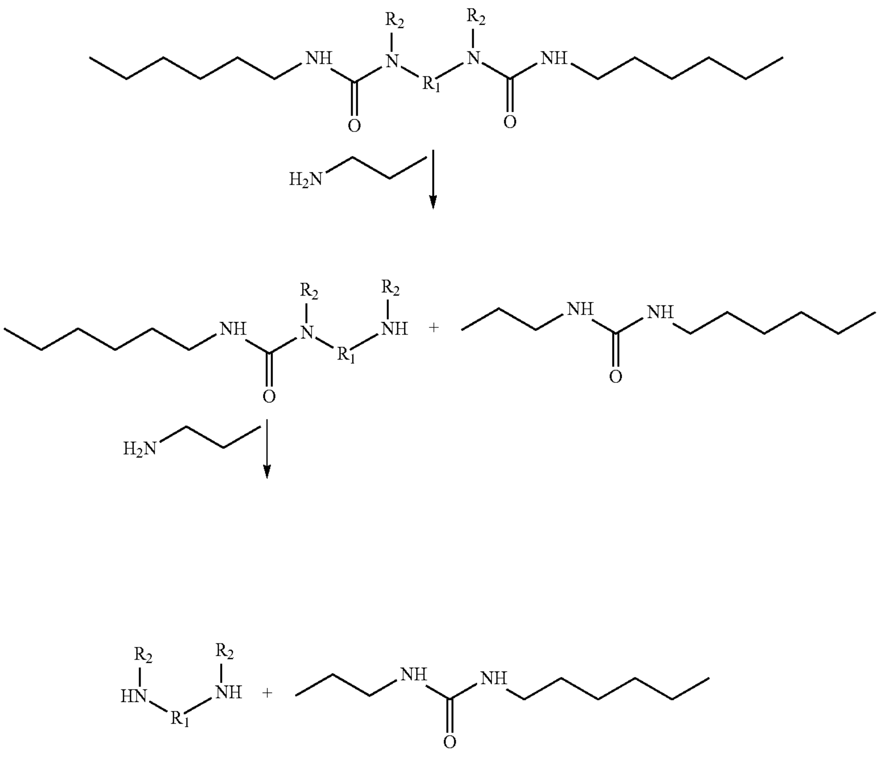

Scheme G

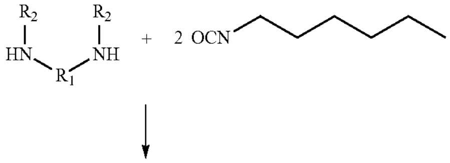

For reasons of comparison, the test series was conducted with those diamines that had performed especially well or badly, respectively, in the preceding foil storage tests of Example 14, i.e. N,N'-di-tert-butylethylenediamine (TBEDA), the chain extender of the TPUUs of Examples 1 to 10, N,N'-diisopropylethylenediamine (IPEDA), that of the TPUU of Example 12, and both diamines piperazine (Pip) and 2,5-dimethylpiperazine (2,5-DMP) known in the art. The syntheses of the corresponding diurea model molecules are described below.

Reference Example 1—TBEDA

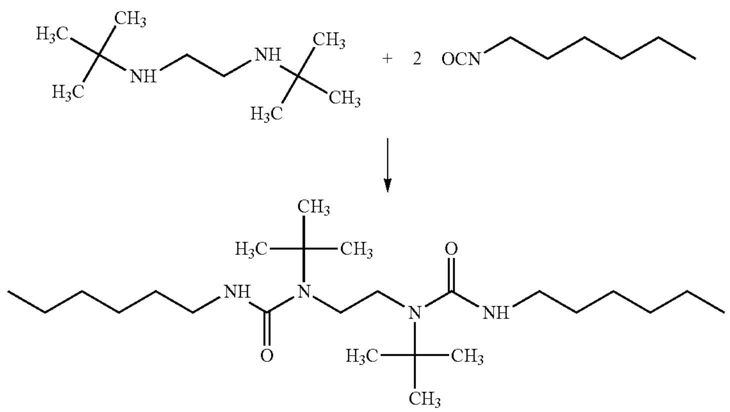

N,N'-Bis(tert-butyl)ethylenediamine was added dropwise to 2.5 equivalents hexyl diisocyanate, dissolved in 5 ml abs. THF, and stirred at room temperature for 24 h. The solvent and the excess reactant were distilled off to quantitatively obtain the respective diurea as pure substance.

$^1$H NMR (400 MHz, acetonitrile-$d_3$) δ [ppm]: 6.18 (s, 2H, NH), 3.25 (s, 4H, $N(CH_3)—CH_2—$), 3.12 (d, J=5.4 Hz, 4H, $N—CH_2$), 1.47 (m, 4H, $N—CH_2—CH_2$), 1.36 (s, 18H, $C(CH_3)_3$), 1.29 (m, 12H, $CH_2$), 0.88 (t, 6H, $CH_3$).

Reference Example 2—IPEDA

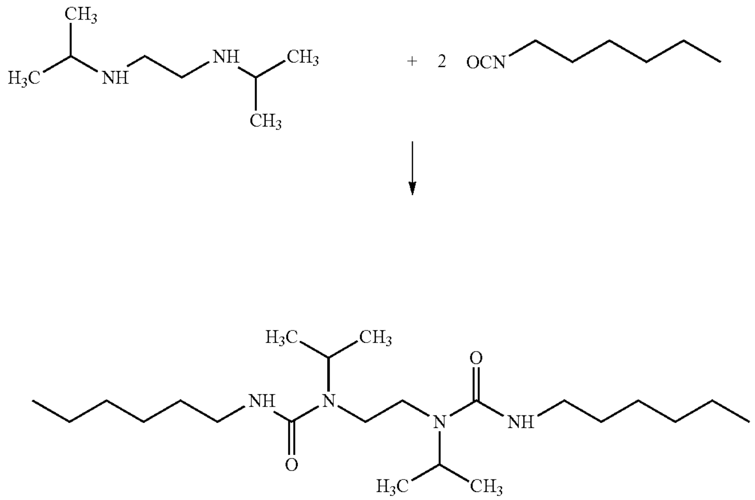

2.5 equivalents of hexyl isocyanate (1 ml, 6.9 mmol) was dissolved in 10 ml abs. THF under argon atmosphere, after which 1 equivalent of N,N'-diisopropylethylenediamine (0.5 ml, 2.8 mmol) was slowly added through a septum using a syringe at room temperature, wherein a slight heat generation was observed. The reaction mixture was stirred at room temperature for 24 h, after which the solvent and excess isocyanate were distilled off to quantitatively obtain 1.07 g (98%) of the desired diurea as pure, slightly yellowish solid.

mp: 97.0-99.5° C.

$^1$H NMR (400 MHz, $CDCl_3$) δ [ppm]: 5.64 (bs, 2H), 4.15 (bs, 2H), 3.25 (q, 4H), 3.09 (s, 4H), 1.54 (qn, 4H), 1.31 (m, 12H), 1.13 (d, 12H), 0.88 (t, 6H).

Reference Example 3—Pip

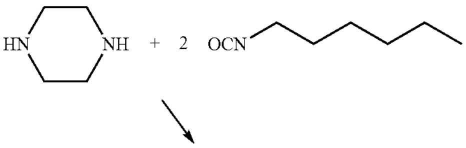

-continued

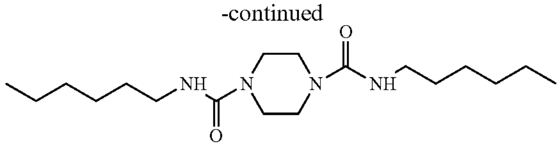

1.00 g piperazine (1 eq.) was weighed in and dried at 0.06 mbar and at room temperature for 1 hour. 50 ml abs. THF was added under argon to dissolve the solid. Then, 4.20 ml (2.5 eq.) hexyl isocyanate was slowly added dropwise, after which the temperature of the reaction mixture increased and a white precipitate was formed. After stirring for 24 h, the solid was removed by filtration, washed with a small amount of dry THF and dried, resulting in 3.18 g (80%) of a white, crystalline solid.

mp: 178.6-181.2° C.

$^1$H NMR (400 MHz, $CDCl_3$) δ [ppm]: 0.88 ppm (t, 6H), 1.29 (m, 12H), 1.50 (qn, 4H), 3.23 (q, 4H), 3.42 (s, 8H), 4.39 (t, 2H).

Reference Example 4—2,5-DMP

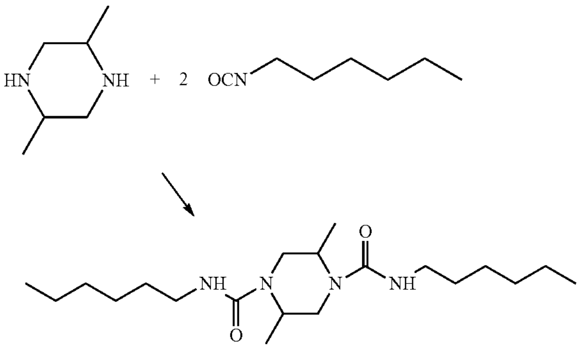

0.50 g dry 2,5-dimethylpiperazine (1 eq.) was dissolved in 25 ml abs. THF under argon atmosphere. Subsequently, 1.6 ml hexyl isocyanate was added dropwise to the stirred solution at room temperature, wherein the solution was heated and a precipitate was formed. After stirring at room temperature for 24 h, the precipitate was removed by filtration, washed with a small amount of dry THF and dried, resulting in 1.16 g (72%) of a white crystalline solid.

mp: 166.1-168.4° C.

$^1$H NMR (400 MHz, $CDCl_3$): δ [ppm]: 4.37 (t, 2H), 4.11 (m, 2H), 3.53-3.16 (8H), 1.50 (m, 4H), 1.30 (m, 12H), 1.18 (d, 6H), 0.89 (t, 6H).

10 to 15 mg of each of these diureas were dissolved in a NMR tube in 0.5 ml $CDCl_3$ and first measured as a pure substance. Subsequently, each volume of a solution of 10.5 μl propylamine in 1 ml $CDCl_3$ was added, so that the molar ratio between diurea and propylamine was 1:1 (±0.1). An initial $^1$H NMR measurement of the mixtures was performed immediately after the preparation (0 d), and further measurements were performed at an interval of 24 h (1 d to 7 d). Between the measurements each NMR tube was stored at room temperature.

Reference Example 1

Figure 6:
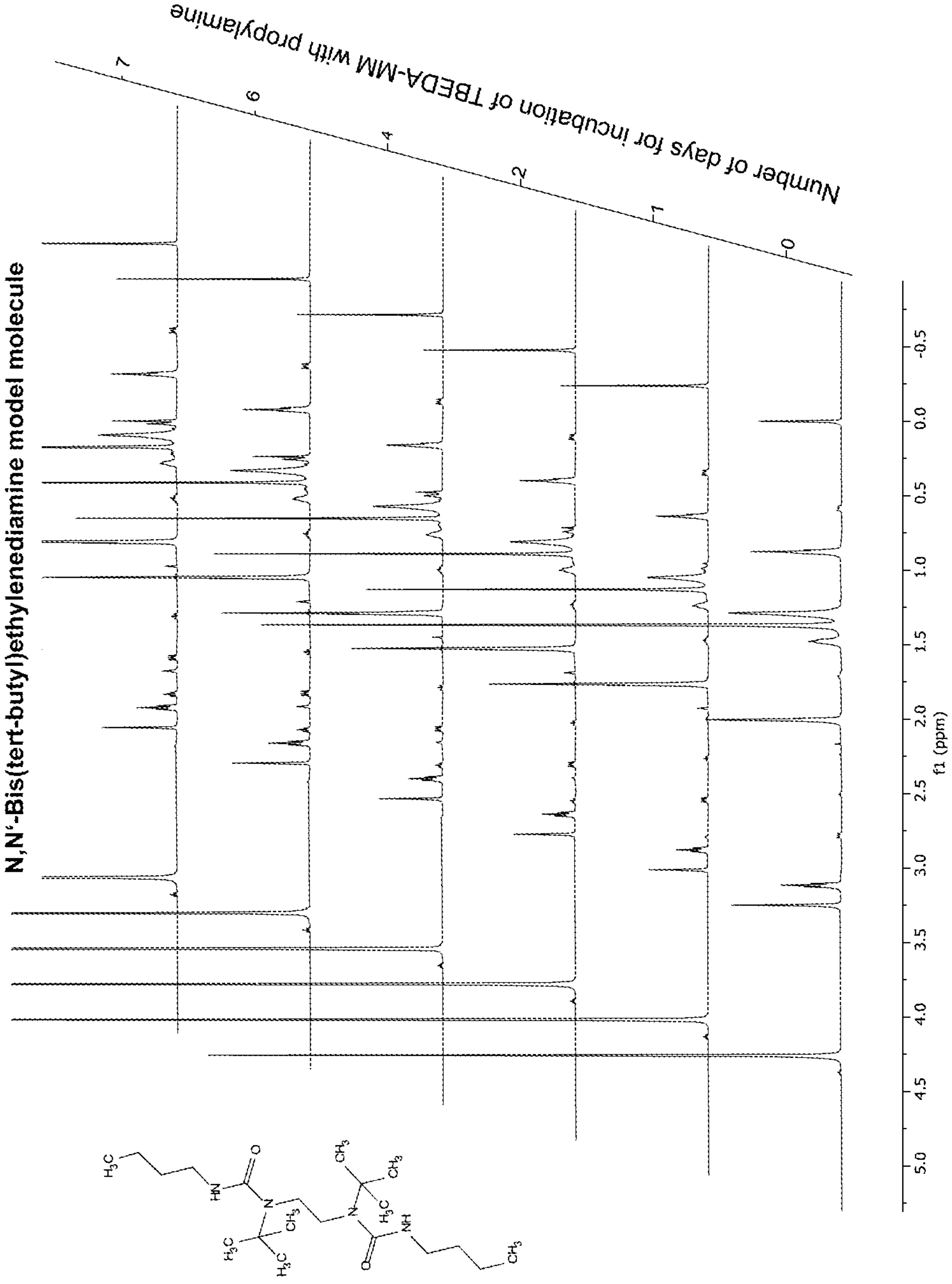
FIGS. 6 to 10 show comparisons of NMR spectra of model substances recorded daily for one week to evaluate sterical hindrance of various secondary diamines.

FIG. 6 shows the sequence of the NMR spectra for the TBEDA diurea for the days 0 to 7 from bottom to top. It is apparent that, in the course of 7 days, several new peaks formed in the ppm range between about 2.5 and 3.4 that continuously increased in intensity.

Figure 7:
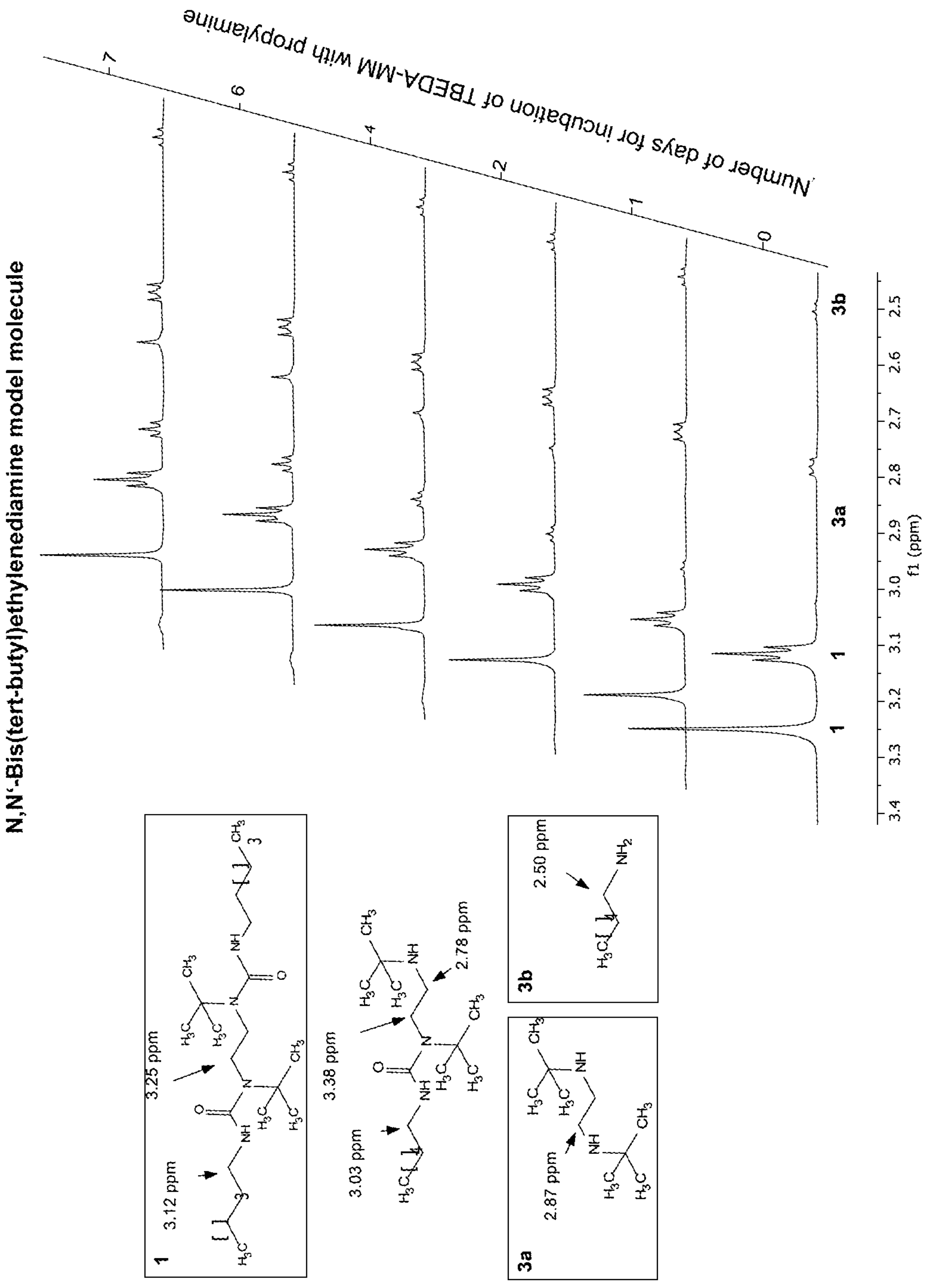

Therefore, FIG. 7 is a magnified depiction of this spectral range and shows the positions of the relevant hydrogen atoms on the newly formed molecules in four pictures.

Picture 1 shows the intact diurea in which the hydrogen atoms of the hexyl radicals appear in an α position relative to the urea groups at 3.12 ppm and those of the central ethylene radical of the diamine appear at 3.25 ppm on the spectrum.

Picture 2 shows the molecule that is formed when, in Scheme H above, an unstable urea bond is eliminated upon reaction of the intermediarily formed isocyanate with propylamine, so only one nitrogen atom of the N,N'-bis(tert-butyl)ethylenediamine is bonded in a urea group and the other one is present as a secondary tert-butylamino group. As a result, the position of the α hydrogens in the hexyl radical shifts from 3.12 to 3.03 ppm, and the position of the hydrogen atoms of the ethylene group shifts from consistent 3.25 ppm to 3.38 ppm in an α position relative to urea or 2.78 ppm in an α position relative to the secondary free amine.

Picture 3a shows the free N,N'-bis(tert-butyl)ethylenediamine that is released upon reaction of the unstable urea group, remaining in the newly formed urea molecule above with another propylamine, the hydrogen atoms of which appear at 2.87 ppm on the spectrum.

Finally, picture 3b shows the position of the hydrogen atoms of propylamine in an α position relative to the amino group at 2.50 ppm.

It is apparent from the $^1$H NMR spectrum on the very bottom that, immediately after mixing the solvent of the diurea model molecule with propylamine, two peaks appeared at 2.78 ppm and 3.03 ppm on day 0 and a third one at 3.38 ppm on day 1 that could be attributed to the mono urea of picture 2. All these peaks gained in intensity in the course of the following days, and from day 2 on, the peak of the hydrogen atoms of the free N,N'-bis(tert-butyl)ethylenediamine can be seen at 2.87 ppm, the intensity of which is constantly increasing afterwards. Accordingly, both reactions with propylamine shown in Scheme H occurred continuously, resulting in the diurea model molecule degrading progressively.

Reference Examples 2 to 4

Figure 8:
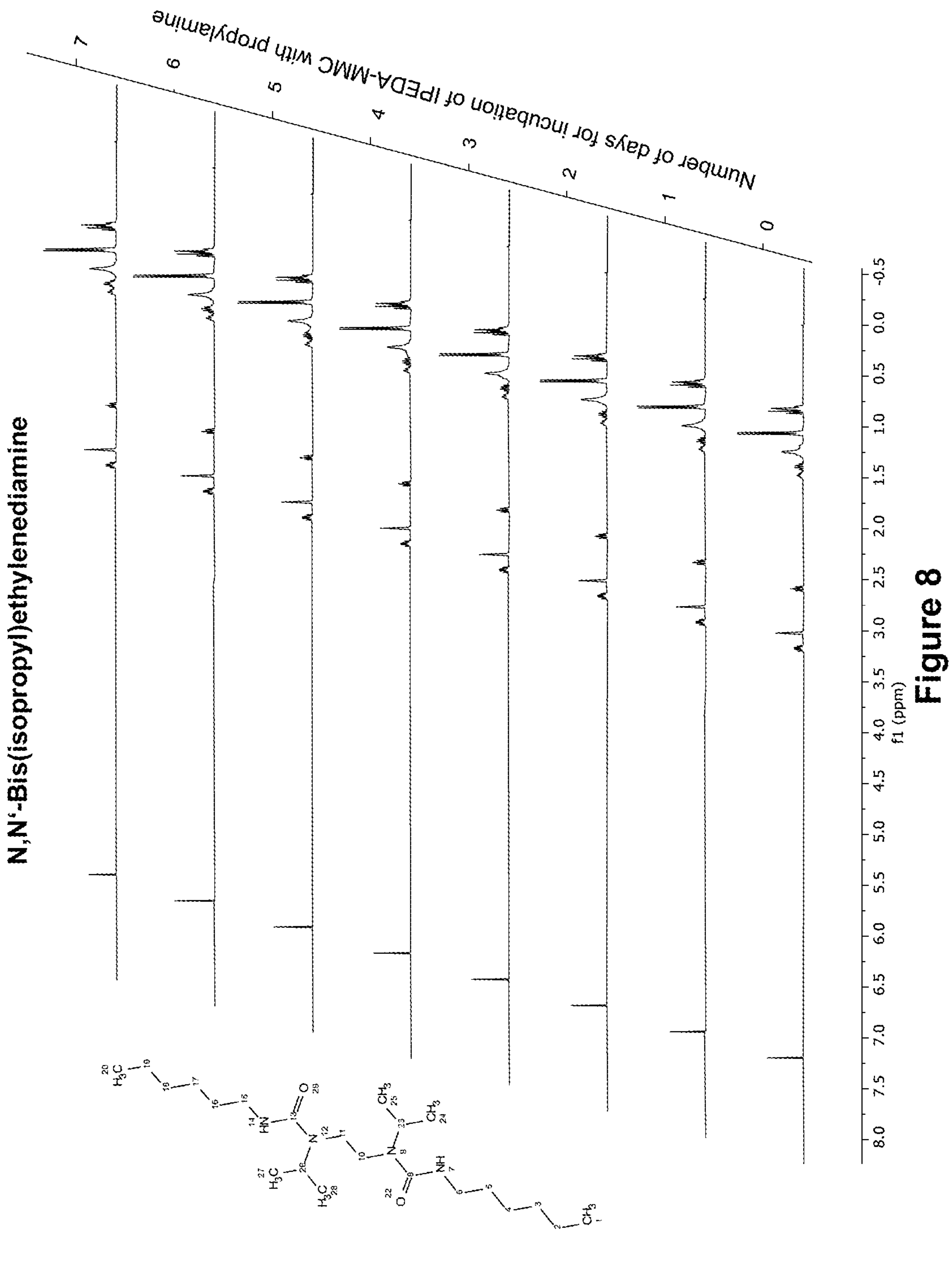
Figure 9:
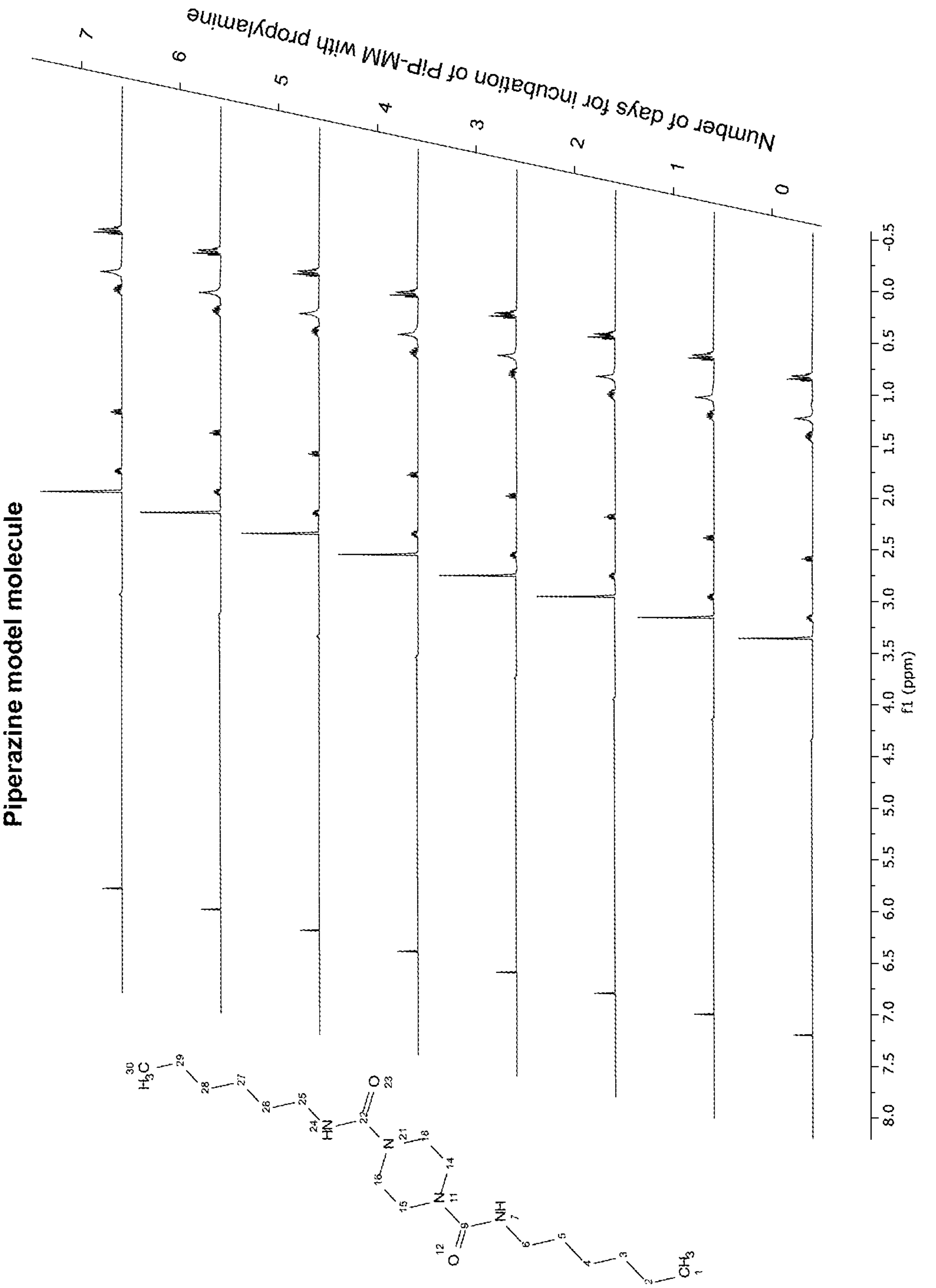
Figure 10:
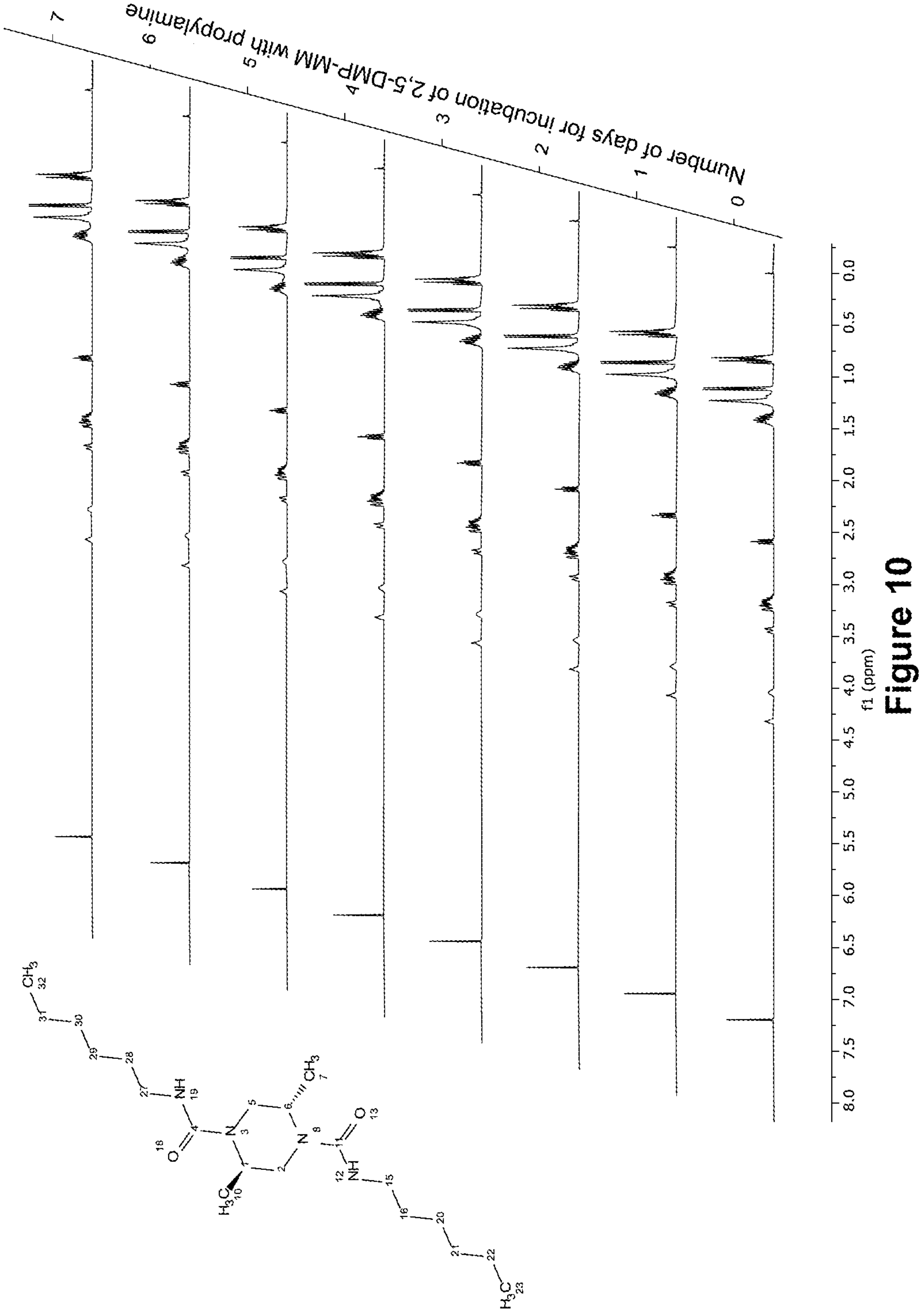

No analogous reactions could be observed for the IPEDA diurea of Reference Example 12, containing the N,N'-diisopropylethylenediamine used in the TPUU of the present invention of Example 12 which—as demonstrated in Table 2 above—only forms unstable urea groups at higher temperatures, or for both piperazine-containing diureas of Reference Examples 3 and 4, i.e. piperazine and 2,5-dimethylpiperazine. FIGS. 8 to 10 clearly show that, in the course of 7 d, the compositions of the three reaction mixtures did not change at all.

Therefore, the results of the Reference Examples 3 and 4 prove once again along with those in Table 2 that piperazine and 2,5-dimethylpiperazine—and with near certainty also the 2-methylpiperazine also known in the art—are not sterically hindered amines according to the present invention.

By using the methodology employed in the present Reference Examples, a person of ordinary skill in the art can relatively easily determine if a particular secondary diamine or a secondary amino alcohol is suited as a chain extender for introducing the radical $C_1$ in a TPUU according to the present invention in advance—without having to prepare the corresponding polyadducts, turn them into foils and test them according to Example 14. In case a certain compound turns out to be unsuitable after having been stored for several days at room temperature another test series can be conducted in which the NMR tube is stored in between measurements at a higher temperature that is primarily limited by the boiling point of the solvent used.

Consequently, it was clearly demonstrated herein that the new thermoplastic poly(urethane-urea) polyadducts according to the invention, having sterically hindered urea groups of formula (I) in a solid state can, by treating them with water, be converted to new polymers, the physical characteristics of which are improved in many ways compared to those of the starting polymers. Therefore, the TPUUs of the invention are ideal for preparing solid products for various applications. Due to their physiological degradability they are especially suited to be used as temporary body implants.

The invention claimed is:

1. A thermoplastic poly(urethane-urea) polyadduct with sterically hindered urea groups having Formula (I):

$$—[I—M—(I—C_1)_a—(I—M)_b—(I—C_2)_c]_n— \quad (I)$$

wherein I, M, $C_1$ and $C_2$ each represent bivalent residues that are linked to each other via a urethane or urea moiety, whereof each I independently represents a bivalent, saturated or unsaturated, aliphatic, alicyclic or aromatic residue with 1 to 20 carbon atoms derived from a diisocyanate;

each M independently represents a bivalent residue of an aliphatic polyether, polyester or polycarbonate derived from a macrodiol having a number average molecular weight $M_n \geq 500$;

each $C_1$ independently represents a bivalent, saturated or unsaturated, aliphatic or alicyclic residue with 1 to 30 carbon atoms derived from a diamine or amino alcohol, each having at least one sterically hindered secondary amino group, through removal of one N-linked hydrogen atom from each nitrogen atom of the diamine or of one N-linked hydrogen atom from the nitrogen atom and the O-linked hydrogen atom from the oxygen atom of the amino alcohol;

each $C_2$ independently represents a bivalent, saturated or unsaturated, aliphatic, alicyclic or aromatic residue with 1 to 20 carbon atoms derived from a diol, diamine or amino alcohol;

wherein, in the residues I, $C_1$ and $C_2$, when more than four carbon atoms are present, optionally at least one of them is substituted by a heteroatom selected from oxygen and nitrogen;

wherein optionally at least one of the residues I, M, Cand $C_2$ comprises one or more ester moieties; and a, b and c each independently represent an integer from 0 to 10, and n is a number ≥3 representing the number of blocks in the polyadduct;

provided that within each separate block a+c≥1 and in all blocks together at least one a≥1 and at least one c≥1.

2. The thermoplastic poly(urethane-urea) polyadduct according to claim 1, wherein:

a and c are each independently ≤5 or ≤3; and/or a and c are each independently ≥1; and/or b≥1; and/or b=c or b=a or b+1=a+c; and/or n≥5 or n≥10 or n≥50.

3. The thermoplastic poly(urethane-urea) polyadduct according to claim 1, wherein at least one of the residues I, M, $C_1$ and $C_2$ comprises one or more ester moieties cleavable under physiological conditions, and that the residues I, M, $C_1$ and $C_2$ as well as any cleavage products thereof are biocompatible and physiologically acceptable.

4. The thermoplastic poly(urethane-urea) polyadduct according to claim 1, wherein the residues I are each independently derived from a diisocyanate selected from the following group: 1,6-hexamethylene diisocyanate, 4,4'-diisocyanatodicyclohexylmethane, isophorone diisocyanate, 1,3-bis(isocyanatomethyl)cyclohexane, diphenylmethane-4,4'-diisocyanate, L-lysine ethyl ester diisocyanate.

5. The thermoplastic poly(urethane-urea) polyadduct according to claim 1, wherein the residues M are each independently derived from a polyether, polyester or polycarbonate selected from the following group: polytetrahydrofuran, polyethylene glycol, polypropylene glycol, polycaprolactone, polylactide, polyglycolide, poly(lactide-co-glycolide), polyhexamethylene carbonate.

6. The thermoplastic poly(urethane-urea) polyadduct according to claim 1, wherein the residues $C_1$ are each independently derived from a diamine and selected from residues of the following Formula (II):

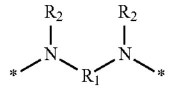

(II)

wherein the bonds marked with asterisks each show the linkage to the carbonyl group of a urea moiety linking the residues I, M, $C_1$ and $C_2$, $R_1$ is selected form bivalent, saturated or unsaturated, aliphatic or alicyclic residues with 1 to 20 carbon atoms; and the $R_2$ are each independently selected from hydrogen and monovalent, optionally bulky, saturated or unsaturated, aliphatic or alicyclic residues with 1 to 10 carbon atoms, provided that not both $R_2$ are simultaneously hydrogen, wherein the two residues $R_2$ are optionally linked to each other and form a ring comprising the two nitrogen atoms, $R_1$, and at least one carbon atoms of the two residues $R_2$;

provided that the ring is not piperazine, 2-methylpiperazine or 2,5-dimethylpiperazine.

7. The thermoplastic poly(urethane-urea) polyadduct according to claim 6, wherein $R_1$ is selected from $C_1$-$C_{10}$-alkylene or $C_4$-$C_{10}$-cycloalkylene residues; and/or the $R_2$ are each independently selected from 1,1-dimethyl-substituted, saturated or unsaturated $C_1$-$C_6$-alkyl residues or 1-methyl-substituted $C_3$-$C_6$-cycloalkyl residues.

8. The thermoplastic poly(urethane-urea) polyadduct according to claim 7, wherein $R_1$ is selected from $C_2$-$C_6$-alkylene or $C_5$-$C_6$-cycloalkylene residues; and/or the $R_2$ are each independently selected from isopropyl, tert-butyl, 1,1-dimethylpropyl or 1-methylcyclohexyl.

9. The thermoplastic poly(urethane-urea) polyadduct according to claim 1, wherein at least one of the residues $C_2$ comprises one or more ester moieties.

10. The thermoplastic poly(urethane-urea) polyadduct according to claim 1, wherein the residues $C_2$ are each independently derived from a diol from the following group: bis(hydroxyethyl) terephthalate, 1,4-butanediol, bis(3-hydroxypropyl) carbonate, 2-hydroxyethyl lactate, neopentyl glycol hydroxypivalate, 2-hydroxyethyl glycolate.

11. The thermoplastic poly(urethane-urea) polyadduct according to claim 1, wherein b+1=a+c and the polyadduct corresponds to the following Formula (IV):

$$—[(I—M—I—C_1)_a—(I—M—I—C_2)_c]_n— \quad (IV)$$

wherein a and c are each independently selected from 1 to 3 or a and c are each 1; and n≥5 or n≥10 or n≥20.

12. A method of performing thermomechanical or solvent-based processes with polymers self-reinforcing on contact with water, the method comprising bringing the thermoplastic poly(urethane-urea) polyadduct according to claim 1 into contact with water.

13. The method according to claim 12, wherein the thermoplastic poly(urethane-urea) polyadduct is processed to a solid product that is exposed to water or an aqueous environment during or after processing in order to improve one or more of its thermomechanical properties.

14. The method according to claim 12, wherein the residues I, M, $C_1$ and $C_2$ of the thermoplastic poly(urethane-urea) polyadduct as well as any cleavage products thereof are biocompatible and physiologically acceptable; and the thermoplastic poly(urethane-urea) polyadduct or the solid product obtained therefrom are usable as biomaterials in biomedical applications.

15. The method according to claim 14, wherein at least one of the residues I, M, $C_1$ and $C_2$ comprises one or more ester moieties cleavable under physiological conditions; and the thermoplastic poly(urethane-urea) polyadduct is used for producing temporary body implants or the solid product obtained therefrom is usable as temporary body implant.

* * * * *